(12) United States Patent
Anand et al.

(10) Patent No.: US 12,607,543 B2
(45) Date of Patent: Apr. 21, 2026

(54) DEVICE FOR ELECTROKINETIC FOCUSING AND ELECTRICAL DETECTION OF PARTICLES AND CHEMICAL SPECIES FACILITATED BY A POROUS ELECTRODE

(71) Applicant: Iowa State University Research Foundation, Inc., Ames, IA (US)

(72) Inventors: Robbyn K. Anand, Ames, IA (US); Beatrise Berzina, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 756 days.

(21) Appl. No.: 17/445,059

(22) Filed: Aug. 13, 2021

(65) Prior Publication Data

US 2022/0050031 A1 Feb. 17, 2022

Related U.S. Application Data

(60) Provisional application No. 62/706,412, filed on Aug. 14, 2020.

(51) Int. Cl.
| | |
|---|---|
| *G01N 1/40* | (2006.01) |
| *A61M 1/16* | (2006.01) |
| *G01N 1/22* | (2006.01) |

(52) U.S. Cl.
CPC ............. *G01N 1/40* (2013.01); *A61M 1/1603* (2014.02); *A61M 1/1656* (2013.01); *G01N 1/2202* (2013.01); *G01N 2001/4038* (2013.01)

(58) Field of Classification Search
CPC ...... G01N 1/40; G01N 1/2202; A61M 1/1656
See application file for complete search history.

(56) References Cited

U.S. PATENT DOCUMENTS

| | | | |
|---|---|---|---|
| 2008/0182136 A1 | 7/2008 | Arnold et al. | |
| 2009/0075393 A1 * | 3/2009 | Lopez .............. | G01N 27/44721 |
| | | | 422/68.1 |
| 2012/0283423 A1 | 11/2012 | Belgrader et al. | |
| 2019/0125951 A1 * | 5/2019 | Anand ................ | A61M 1/1678 |
| 2020/0255881 A1 * | 8/2020 | Watkins ................ | C12N 11/06 |

OTHER PUBLICATIONS

Leinweber et al., "Nonequilibrium Electrokinetic Effects in Beds of Ion-Permselective Particles", 2004, Langmuir, 20, 11637-11648 (Year: 2004).*

(Continued)

*Primary Examiner* — Maris R Kessel
*Assistant Examiner* — Mickey Huang
(74) *Attorney, Agent, or Firm* — McKee, Voorhees & Sease, PLC

(57) ABSTRACT

High-throughput microfluidic devices comprising one or more fluidic microchannels each with at least one flow-through 3D structure comprising a 3D electrode, or alternatively a 3D permselective structure, and optional secondary bead bed(s) are disclosed. Such devices can be used for counter-flow focusing of charged species via ion concentration polarization and in situ quantification of electrokinetically enriched charged species from an ionically conductive solution by both optical and electrical detection.

19 Claims, 17 Drawing Sheets
(17 of 17 Drawing Sheet(s) Filed in Color)

Specification includes a Sequence Listing.

(56)　　　　　References Cited

OTHER PUBLICATIONS

Cheow et al., Massively parallel concentration device for multiplexed immunoassays, 2011, Lab Chip, 2011, 11, 1351 (Year: 2011).*

Thomas et al., Selective trace enrichment by immunoaffinity capillary electrochromatography on-line with capillary zone electrophoresis—laser-induced fluorescence, Electrophoresis, Jan. 1999;20(1):57-66. (Year: 1999).*

Anand et al., "Bipolar electrode focusing: tuning the electric field gradient", Lab Chip, vol. 11, pp. 518-527, 2011.

Anand et al., "Bipolar Electrode Focusing: Faradaic Ion Concentration Polarization", Analytical Chemistry, vol. 83, pp. 2351-2358, dx.doi.org/10.1021/ac103302j, 2011.

Cheow et al., "Increasing the Sensitivity of Enzyme-Linked Immunosorbent Assay Using Multiplexed Electrokinetic Concentrator", Analytical Chemistry, vol. 82, pp. 3383-3388, Apr. 15, 2010.

Deng et al., "A Novel Thermal Bubble Valve Integrated Nanofluidic Preconcentrator for Highly Sensitive Biomarker Detection", ACS Sensors, vol. 3, pp. 1409-1415, 2018.

Hlushkou et al., "Electric field gradient focusing in microchannels with embedded bipolar electrode", Lab Chip, vol. 9, pp. 1903-1913, DOI: 10.1039/b822404h, 2009.

Huh et al., "Surface Conduction and Electroosmotic Flow around Charged Dielectric Pillar Arrays in Microchannels", Manuscript ID LC-ART-10-2019-001008, Lab on a Chip, pp. 1-41, Oct. 11, 2019.

Huh et al., "Surface Conduction and Electroosmotic Flow around Charged Dielectric Pillar Arrays in Microchannels", Lab on a Chip, Issue 3, pp. 1-6, 2020.

Kim et al., "Stabilization of ion concentration polarization layer using micro fin structure for high-throughput applications", Nanoscale, vol. 9, pp. 3466-3475, 2017.

Ko et al., "Massively parallel concentration device for multiplexed immunoassays", Lab Chip, vol. 11, pp. 1351-1358, 2011.

Kwak et al., "Half-Cell Ion Concentration Polarization on Nafion-Coated Electrode", Journal of Physical Chemistry Letters, vol. 9, pp. 2991-2999, 2018.

Leinweber et al., "Nonequilibrium Electrokinetic Effects in Beds of Ion-Permselective Particles", Langmuir, vol. 20, pp. 11637-11648, 2004.

Ramshani et al., "Extracellular vesicle microRNA quantification from plasma using an integrated microfluidic device", Communications Biology, vol. 2, No. 189, pp. 1-10, https://doi.org/10.1038/s42003-019-0435-1, 2019.

Senapati et al., "An ion-exchange nanomembrane sensor for detection of nucleic acids using a surface charge nversion phenomenon", Biosensors and Bioelectronics, vol. 60, pp. 92-100, 2014.

Slouka et al., "Integrated, DC voltage-driven nucleic acid diagnostic platform for real sample analysis: detection of oral cancer", Talanta, vol. 145, pp. 35-42, DOI: 10.1016/j.talanta.2015.04.083, Dec. 1, 2015.

Syed et al., "Creating Sub-50 nm Nanofluidic Junctions in PDMS Microchip via Self-Assembly Process of Colloidal Silica Beads for Electrokinetic Concentration of Biomolecules", Lab Chip, vol. 14, No. 23, pp. 4455-4460, doi:10.1039/c4lc00895b., Dec. 7, 2014.

Taller et al., "On-Chip Surface Acoustic Wave Lysis and Ion-Exchange Nanomembrane Detection of Exosomal RNA for Pancreatic Cancer Study and Diagnosis", Lab Chip, vol. 15, Issue 7, pp. 1656-1666, doi: 10.1039/c5lc00036j., Apr. 7, 2015.

Wang et al., "Pre-binding dynamic range and sensitivity enhancement for immuno-sensors using nanofluidic preconcentrator", Lab on a Chip, Issue 3, pp. 1-6, https://doi.org/10.1039/B717220F, 2008.

Yin et al., "A non-optical multiplexed PCR diagnostic platform for serotype-specific detection of dengue virus", Sensors & Actuators: B. Chemical, vol. 310, pp. 1-10, DOI: 10.1016/j.snb.2020.127854, 2020.

Kim et al., "Ion concentration polarization in a single and open microchannel induced by a surface-patterned perm-selective film", Analyst, vol. 138, No. 5, pp. 1273-1604, Mar. 7, 2013.

Dhopeshwarkar et al., "Electrokinetics in Microfluidic Channels Containing a Floating Electrode", Journal of American Chemical Society, vol. 130, pp. 10480-10481, 2008.

Anand et al., "Negative Dielectrophoretic Capture and Repulsion of Single Cells at a Bipolar Electrode: The Impact of Faradaic Ion Enrichment and Depletion", JACS, vol. 137, pp. 776-783, Jan. 6, 2015.

Anand et al., "Bipolar Electrode Focusing: Faradaic Ion Concentration Polarization", Analytical Chemistry, vol. 83, pp. 2351-2358, 2011.

Balster et al., "Morphology and Microtopology of Cation-Exchange Polymers and the Origin of the Overlimiting Current", J. Phys. Chem. B., vol. 111, pp. 2152-2165, 2007.

Breadmore et al., "Recent advances in enhancing the sensitivity of electrophoresis and electrochromatography in capillaries and microchips", Electrophoresis, vol. 36, pp. 36-61, 2015.

Cheow et al., "Continuous Signal Enhancement for Sensitive Aptamer Affinity Probe Electrophoresis Assay Using Electrokinetic Concentration", Anal. Chem., vol. 83(18), pp. 7086-7093, Sep. 15, 2011.

Cheow et al., "Detecting Kinase Activities from Single Cell Lysate Using Concentration-Enhanced Mobility Shift Assay", Analytical Chemistry, 86, pp. 7455-7462, 2014.

Crooks, Richard M., Principles of Bipolar Electrochemistry, ChemElectroChem, vol. 3, pp. 357-359, 2016.

Davies et al., "Continuous Redirection and Separation of Microbeads by Faradaic Ion Concentration Polarization", ChemElectroChem, author's manuscript, 38 pages, 2018.

Davies et al., "Focusing, sorting, and separating microplastics by serial faradaic ion concentration polarization", Chemical Science, vol. 11, pp. 5547-5558, 2020.

De Valenca et al., "Confined Electroconvective Vortices at Structured Ion Exchange Membranes", Langmuir, vol. 34, pp. 2455-2463, 2018.

Fosdick et al., "Bipolar Electrochemistry", Angew. Chem. Int. Ed., vol. 52, pp. 10438-10456, 2013.

Hong et al., "Electrochemical detection of methylated DNA on a microfluidic chip with nanoelectrokinetic pre-concentration", Biosensors and Bioelectronics, vol. 107, pp. 103-110, 2018.

Kim et al., "Ion Concentration Polarization by Bifurcated Current Path", Scientific Reports, pp. 1-12, Jul. 11, 2017.

Kim et al., "Concentration Polarization and Nonlinear Electrokinetic Flow near Nanofluidic Channel", Phys. Rev. Lett., vol. 99(4), 9 pages, Jul. 27, 2007.

Knust et al., "Dual-channel bipolar electrode focusing: simultaneous separation and enrichment of both anions and cations", 12, pp. 4107-4114, 2012.

Koefoed et al., "Bipolar electrochemistry—A wireless approach for electrode reactions", Current Opinion in Electrochemistry, vol. 2, pp. 13-17, 2017.

Kwak et al., "Continuous-Flow Biomolecule and Cell Concentrator by Ion Concentration Polarization", Analytical Chemistry, vol. 83, pp. 7348-7355, 2011.

Laws et al., "Bipolar Electrode Focusing: Simultaneous Concentration Enrichment and Separation in a Microfluidic Channel Containing a Bipolar Electrode", Anal. Chem., vol. 81, pp. 8923-8929, 2009.

Lee et al., "dCas9-mediated Nanoelectrokinetic Direct Detection of Target Gene for Liquid Biopsy", Nano Letters, vol. 18, pp. 7642-7650, 2018.

Lee, Jeong Hoon, "Microfluidic Concentration-Enhanced Cellular Kinase Activity Assay", Journal of the American Chemical Society, 3 pages, 2009.

Li et al., "Recent advancements in ion concentration polarization", Analyst, vol. 141, pp. 3496-3510, 2016.

Li et al., "Faradaic Ion Concentration Polarization on a Paper Fluidic Platform", Analytical Chemistry, vol. 89, pp. 4294-4300, Mar. 17, 2017.

Lu et al., "Ion concentration polarization (ICP) of proteins at silicon micropillar nanogaps", PLos One, vol. 14(11), 12 pages, Nov. 4, 2019.

Macdonald et al., "Out-of-plane ion concentration polarization for scalable water desalination", Lab on a Chip, vol. 14, pp. 681-685, 2014.

(56)        References Cited

OTHER PUBLICATIONS

Maletzki et al., "Ion transfer across electrodialysis membranes in the overlimiting current range: stationary voltage current characteristics and current noise power spectra under different conditions of free convection", Journal of Membrane Science, vol. 71, pp. 105-115, 1992.

Mani et al., "On the Propagation of Concentration Polarization from Microchannel-Nanochannel Interfaces Part I. Analytical Model and Characteristic Analysis", Langmuir, vol. 25(6), pp. 3898-3908, Apr. 9, 2009.

Marczak et al., "Simultaneous isolation and preconcentration of exosomes by ion concentration polarization", Electrophoresis, vol. 39, pp. 2029-2038, 2018.

Ouyang et al., "Universal amplification-free molecular diagnostics by billion-fold hierarchical nanofluidic concentralion", PNAS, vol. 116, No. 33, 10 pages, Aug. 13, 2019.

Ouyang et al., "Theoretical Limits and Scaling Laws for Electrokinetic Molecular Concentration via Ion Concentration Polarization", 10, 15187-15194, 2018.

Papadimitriou et al., "Free Flow Ion Concentration Polarization Focusing (FF-ICPF)", Analytical Chemistry, vol. 92, pp. 4866-4874, 2020.

Park et al., "Combining dielectrophoresis and concentration polarization-based preconcentration to enhance bead-based immunoassay sensitivity", Nanoscale, vol. 11, pp. 9436-9443, 2019.

Perdue et al., "Bipolar Electrode Focusing: The Effect of Current and Electric Field on Concentration Enrichment", Anal. Chem., vol. 81, pp. 10149-10155, 2009.

Rubinstein et al., "Voltage against Current Curves of Cation Exchange Membranes", J. Chem. Soc. Faraday Trans. 2 Mol. Chem. Phys., vol. 75(6), pp. 231-246, 1979.

Senapati et al., "An ion-exchange nanomembrane sensor for detection of nucleic acids using a surface charge inversion phenomenon", Biosensors and Bioelectronics, vol. 60, pp. 92-100, 2014.

Song et al., "Concurrent DNA Preconcentration and Separation in Bipolar Electrode-Based Microfluidic Device", Anal. Methods, vol. 7(4), pp. 1273-1279, 2015.

Wang et al., "Million-fold Preconcentration of Proteins and Peptides by Nanofluidic Filter", Anal. Chem., vol. 77, pp. 4293-4299, 2005.

Wang et al., "Pre-binding dynamic range and sensitivity enhancement for immuno-sensors using nanofluidic preconcentrator", Lab on a Chip, vol. 8, No. 3, pp. 392-394, Mar. 2008.

Yin et al., "A non-optical multiplexed PCR diagnostic platform for serotype-specific detection of dengue virus", Sensors & Actuators B: Chemical, vol. 310, 10 pages, 2002.

Yossifon et al., "Eliminating the limiting-current phenomenon by geometric field focusing into nanopores and nanoslots", Physical Review E, vol. 81, 13 pages, 2010.

Yossifon et al., "Nonlinear current-voltage Characteristics of nanochannels", Physical Review E, vol. 79, 9 pages, 2009.

Zangle et al., "Theory and experiments of concentration polarization and ion focusing at microchannel and nanochannel interfaces", Chem. Soc. Rev., vol. 39, pp. 1014-1035 2009.

Zhang et al., "A bifurcated continuous field-flow fractionation (BCFFF) chip for high-yield and high throughput nucleic acid extraction and purification", Lab on a Chip, vol. 19, pp. 3853-3861, 2019.

* cited by examiner

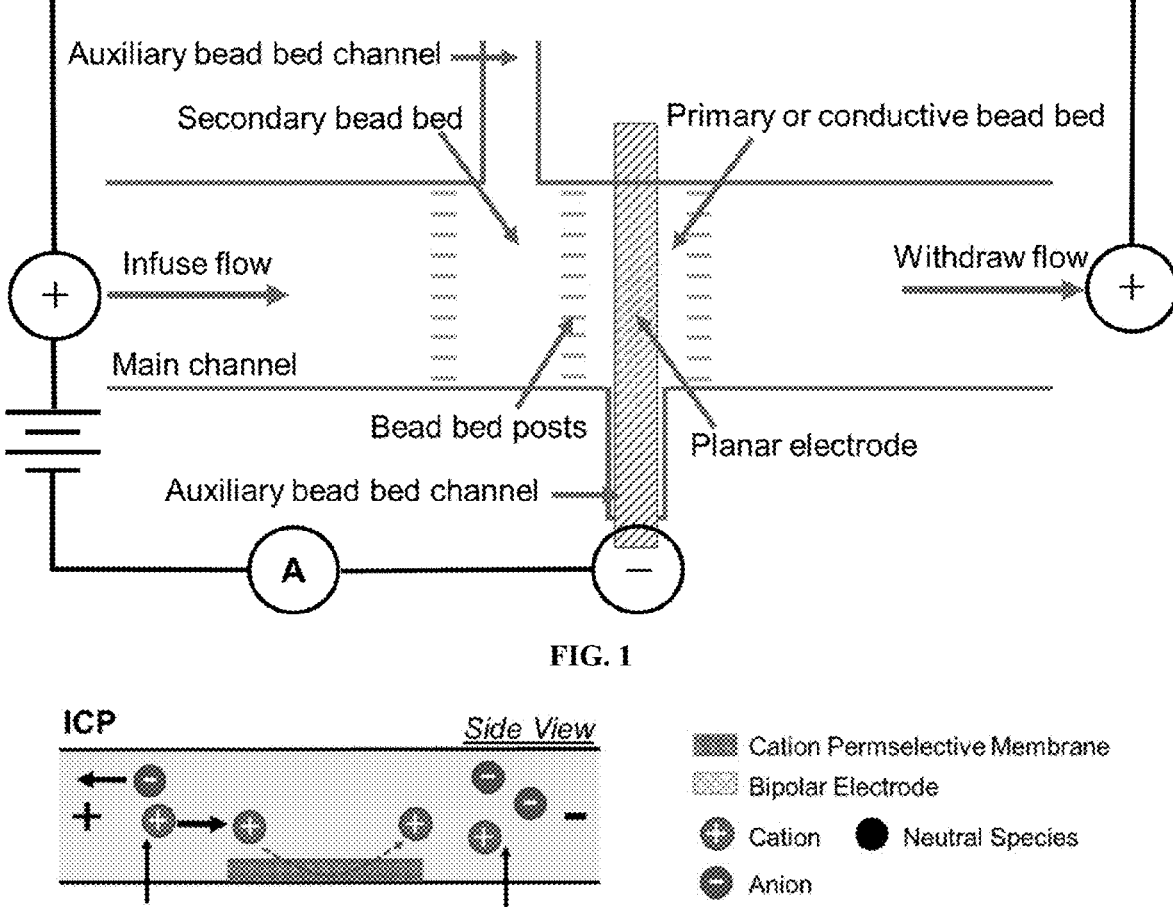
FIG. 1
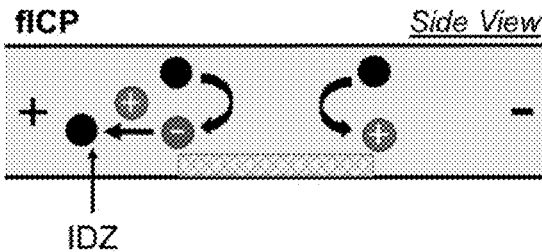
FIG. 2A
FIG. 2B

—■— Prior to the experiment
—●— Target and 2° probe, with enrichment
—▲— 2° probe only, with enrichment
—▼— Target and 2° probe, without enrichment
—◆— After regeneration Inlet      Bead Bed Auxiliary Inlet Channels      Outlet

SEQUENCE LISTING

```
<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: Probe

<400> SEQUENCE: 1
atataaagaa gtacttctgg agtg                                          24

<210> SEQ ID NO 2
<211> LENGTH: 24
<212> TYPE: DNA
<213> ORGANISM: Artificial Sequence
<220> FEATURE:
<223> OTHER INFORMATION: Probe

<400> SEQUENCE: 2
agatcgatgt ctctttagag ctac                                          24

<210> SEQ ID NO 3
<211> LENGTH: 70
<212> TYPE: DNA
<213> ORGANISM: Homo sapiens

<400> SEQUENCE: 3
tatatttctt catgaagacc tcacagtaaa aataggtgat tttggtctag ctacagagaa    60
atctcgatgg                                                          70
```

-continued

```
<210> SEQ ID NO 4
<211> LENGTH: 210
<212> TYPE: DNA
<213> ORGANISM: Homo sapiens

<400> SEQUENCE: 4
tatatttctt catgaagacc tcacagtaaa aataggtgat tttggtctag ctacagagaa          60
atctcgatgg agtgggtccc atcagtttga acagttgtct ggatccattt tgtggatggt         120
aagaattgag gctatttttc cactgattaa atttttggcc ctgagatgct gctgagttac         180
tagaaagtca ttgaaggtct caactatagt                                          210

<210> SEQ ID NO 5
<211> LENGTH: 24
<212> TYPE: DNA
<213> ORGANISM: Artificial Sequence
<220> FEATURE:
<223> OTHER INFORMATION: Probe

<400> SEQUENCE: 5
gtgaggtctt catgaagaaa tata                                                 24

<210> SEQ ID NO 6
<211> LENGTH: 200
<212> TYPE: DNA
<213> ORGANISM: Homo sapiens

<400> SEQUENCE: 6
tatatttctt catgaagacc tcacagtaaa aataggtgat tttggtctag ctacagagaa          60
atctcgatgg agtgggtccc atcagtttga acagttgtct ggatccattt tgtggatggt         120
aagaattgag gctatttttc cactgattaa atttttggcc ctgagatgct gctgagttac         180
tagaaagtca ttgaaggtct                                                     200

<210> SEQ ID NO 7
<211> LENGTH: 24
<212> TYPE: DNA
<213> ORGANISM: Artificial Sequence
<220> FEATURE:
<223> OTHER INFORMATION: Probe

<400> SEQUENCE: 7
catcgagatt tctctgtagc taga                                                 24
```

DEVICE FOR ELECTROKINETIC FOCUSING AND ELECTRICAL DETECTION OF PARTICLES AND CHEMICAL SPECIES FACILITATED BY A POROUS ELECTRODE

CROSS-REFERENCE TO RELATED APPLICATIONS

This application claims priority under 35 U.S.C. § 119 to provisional application Ser. No. 62/706,412, filed Aug. 14, 2020, herein incorporated by reference in its entirety.

GOVERNMENT RIGHTS

This invention was made with government support under National Science Foundation Grant No. CHE1849109. The government has certain rights in this invention.

SEQUENCE LISTING

The instant application contains a Sequence Listing which has been submitted in ASCII format by electronic submission and is hereby incorporated by reference in its entirety. Said ASCII copy, created on Jun. 8, 2021, is named ANAND_P13288US01_SEQLISTING_ST25.txt and is 4,096 bytes in size.

FIELD OF THE INVENTION

The present invention is related to a high-throughput microfluidic device and methods for counter-flow focusing of charged species via ion concentration polarization. Specifically, a microfluidic device that comprises one or more fluidic microchannels each with at least one flow-through 3D structure comprising a 3D electrode, or alternatively a 3D permselective structure, and optional secondary bead bed(s). Such a microfluidic device is capable of in situ quantification of electrokinetically enriched charged species from an ionically conductive solution by both optical and electrical detection.

BACKGROUND OF THE INVENTION

Point-of-care ("POC") testing allows for rapid detection, monitoring, and management of disease and is especially important in hospitals, clinics and remote areas where healthcare facilities and personnel are limited. However, biomarkers that serve as indicators for disease detection are often present at a low concentration (fM-pM) and therefore, require preconcentration. Electrokinetic methods of analyte preconcentration are advantageous for integration with POC testing because they provide efficient transport of charged species in small sample volumes.

Over the past two decades, electrokinetic methods of focusing that employ ion concentration polarization ("ICP") as illustrated in FIG. 2A and faradaic ICP ("fICP") as illustrated in FIG. 2B have been developed for enrichment and separation of a wide range of disease biomarkers, including nucleic acids (Ouyang, W.; Han, J., Universal Amplification-Free Molecular Diagnostics by Billion-Fold Hierarchical Nanofluidic Concentration. *Proc. Natl. Acad. Sci.* 2019, 116 (33), 16240-16249; Song, H.; Wang, Y.; Garson, C.; Pant, K., Concurrent DNA Preconcentration and Separation in Bipolar Electrode-Based Microfluidic Device. *Anal. Methods* 2015, 7 (4), 1273-1279; Hong, S. A.; Kim, Y.-J.; Kim, S. J.; Yang, S. Electrochemical Detection of Methylated DNA on a Microfluidic Chip with Nanoelectrokinetic Pre-Concentration. *Biosens. Bioelectron.* 2018, 107, 103-110.), proteins (Wang, Y. C.; Stevens, A. L.; Han, J. Million-Fold Preconcentration of Proteins and Peptides by Nanofluidic Filter. *Anal. Chem.* 2005, 77 (14), 4293-4299; Cheow, L. F.; Han, J. Continuous Signal Enhancement for Sensitive Aptamer Affinity Probe Electrophoresis Assay Using Electrokinetic Concentration. *Anal. Chem.* 2011, 83 (18), 7086-7093.), enzymes (Jeong, H. L.; Cosgrove, B. D.; Lauffenburger, D. A.; Han, J. Microfluidic Concentration-Enhanced Cellular Kinase Activity Assay. *J. Am. Chem. Soc.* 2009, 131 (30), 10340-10341; Cheow, L. F.; Sarkar, A.; Kolitz, S.; Lauffenburger, D.; Han, J. Detecting Kinase Activities from Single Cell Lysate Using Concentration-Enhanced Mobility Shift Assay. *Anal. Chem.* 2014, 86 (15), 7455-7462.), exosomes (Marczak, S.; Richards, K.; Ramshani, Z.; Smith, E.; Senapati, S.; Hill, R.; Go, D. B.; Chang, H. C. Simultaneous Isolation and Preconcentration of Exosomes by Ion Concentration Polarization. *Electrophoresis* 2018, 39 (15), 2029-2038.), and biological cells (Kim, M.; Jia, M.; Kim, T. Ion Concentration Polarization in a Single and Open Microchannel Induced by a Surface-Patterned Perm-Selective Film. *Analyst* 2013, 138 (5), 1370; Kwak, R.; Kim, S. J.; Han, J., Continuous-Flow Biomolecule and Cell Concentrator by Ion Concentration Polarization. *Anal. Chem.* 2011, 83 (19), 7348-7355; Anand, R. K.; Johnson, E. S.; Chiu, D. T., Negative Dielectrophoretic Capture and Repulsion of Single Cells at a Bipolar Electrode: The Impact of Faradaic Ion Enrichment and Depletion. *J. Am. Chem. Soc.* 2015, 137 (2), 776-783.) Concentration enrichment ranging from $10^2$-fold for simple devices to even $10^9$-fold for multistage hierarchical preconcentrators has been reported.

However, despite the success of these preconcentration methods, some aspects remain challenging. Many existing ICP-based preconcentrators operate at >100 V, which hinders integration into POC devices, as a device that requires such a voltage cannot be powered by a common battery. Further, there is still the need for improvement of volumetric throughput, integration with downstream analysis, and the development of strategies to decrease fluidic instability. Fluidic instability, or vortex flow, which is exacerbated by increased device dimensions, leads to unwanted mixing, ultimately limiting sensitivity.

For instance, existing fICP preconcentrators use thin film electrodes to facilitate electrochemical reactions that generate an ion depleted zone ("IDZ"). However, in a tall microchannel or under rapid fluid flow, the IDZ does not extend the full height of the microchannel from the planar electrode. Therefore, a fraction of the analyte escapes, carried over the IDZ by convection. This phenomenon decreases the efficiency of enrichment. Hlushkou, D.; Perdue, R. K.; Dhopeshwarkar, R.; Crooks, R. M.; Tallarek, U., Electric Field Gradient Focusing in Microchannels with Embedded Bipolar Electrode. *Lab Chip* 2009, 9 (13), 1903-1913. This challenge has been addressed by decreasing the microchannel height and also by increasing the applied electric field to augment the IDZ size. Anand, R. K.; Sheridan, E.; Knust, K. N.; Crooks, R. M. Bipolar Electrode Focusing: Faradaic Ion Concentration Polarization., *Anal. Chem.* 2011, 83 (6), 2351-2358. However, these approaches sacrifice volumetric throughput and are limited by gas bubble formation, respectively. MacDonald et. al. achieved a throughput of up to 20 $\mu L\,min^{-1}$ by using an out-of-plane device, in which a vertical nanoporous membrane was integrated into the wall of a microchannel, thereby increasing the exposed area available for ion transport. Out-of-Plane Ion Concentration Polarization for Scalable Water Desalination. *Lab Chip* 2014, 14 (4), 681-685.

Electrokinetic enrichment of biomolecules has been shown to increase the sensitivity of bead-based immunoassays. Wang et al. reported an approximate 500-fold increase in the sensitivity of R-phycoerythrin protein detection following 30 minutes of preconcentration followed by a 30-minute binding step to antibody-modified particles. Pre-Binding Dynamic Range and Sensitivity Enhancement for Immuno-Sensors Using Nanofluidic Preconcentrator. *Lab Chip* 2008, 8 (3), 392-394. In related work, Park and coworkers developed a platform combining dielectrophoretic capture of freely suspended biotin-conjugated beads with an ICP based preconcentration step. This approach increased the sensitivity for detection of avidin at biotin-conjugated particles by 3-fold and opened a route to control bead positioning for localized sensor development. Combining Dielectrophoresis and Concentration Polarization-Based Preconcentration to Enhance Bead-Based Immunoassay Sensitivity. *Nanoscale* 2019, 11 (19), 9436-9443. Most recently, Lu et al. reported 162-fold enhanced sensitivity for fluorescently-tagged inflammatory cytokines using a silicon nanogap preconcentrator. Ion Concentration Polarization (ICP) of Proteins at Silicon Micropillar Nanogaps. *PLoS One* 2019, 14 (11), 1-17. These results demonstrate that ICP-based preconcentration can enhance the speed and sensitivity of immunoassays, which is advantageous for POC applications. Nevertheless, these assays are limited in scope because they require the analyte to be fluorescent or to be tagged with a fluorescent label.

Senapati et al. developed a label-free non-optical sensor, which employs ICP itself as a reporting mechanism. An Ion-Exchange Nanomembrane Sensor for Detection of Nucleic Acids Using a Surface Charge Inversion Phenomenon. *Biosens. Bioelectron.* 2014, 60, 92-100. Ion selective structures exhibit distinct non-linear current-voltage characteristics. These authors showed that binding of nucleic acids on the surface of an ion permselective membrane produces a change in ionic current and, in turn, causes a shift in the current-voltage curve ("CVC"). This sensor was operated by simply incubating the sample with the membrane for a period of 15 minutes prior to reading the CVC with no electrokinetic preconcentration step. This procedure resulted in a detection limit in the range of 10-100 nM for a 27 bp sequence for a 3.5 mm$^2$ and 1 pM for a 1 mm$^2$ sensor. Chang and coworkers developed this approach further, demonstrating sensitive and selective detection of four dengue virus serotypes following RNA extraction from blood plasma and amplification by reverse transcriptase polymerase chain reaction ("RT-PCR"). A Non-Optical Multiplexed PCR Diagnostic Platform for Serotype-Specific Detection of Dengue Virus. *Sensors Actuators, B Chem.* 2020, 310 (February), 127854. It is notable that there was still no electrokinetic pre-enrichment step. The limit of detection for the combination of RT-PCR and the sensor was 100 copies of viral RNA per 1 mL of plasma. The key point is that these detection limits are competitive with fluorescence-based methods but require only simple electrical equipment.

For many such biomedical applications, sensitivity is limited by the volume of fluid that can be 'swept' for the analyte within a reasonable timeframe. Fluidic instability is the primary limitation to scaling devices up for increased volumetric throughput. When the channel cross section becomes large, mixing driven by fluid vortices drastically decreases the efficiency of enrichment and separation. To understand how to mitigate this detrimental process, several research groups have proposed theoretical models describing mechanisms for vortex flow formation indicating that the dominant mechanism can vary based on the critical dimensions of microchannel and the concentration of background electrolyte.

Experimental approaches have been developed to control vortex formation, including geometric constriction of the fluid in microslits, creation of an alternative current path through the IDZ by coating the channel with a highly conductive polymer, and addition of microposts to augment surface conduction within the IDZ. Kim, K.; Kim, W.; Lee, H.; Kim, S. J. Stabilization of Ion Concentration Polarization Layer Using Micro Fin Structure for High-Throughput Applications. *Nanoscale* 2017, 9 (10), 3466-3475; Kim, J.; Cho, I.; Lee, H.; Kim, S. J. Ion Concentration Polarization by Bifurcated Current Path. *Sci. Rep.* 2017, 7 (1), 1-12.

Chang and coworkers have further demonstrated that increased surface area of a permselective membrane leads to smaller vortices due to a decrease in the current demand per area. Eliminating the Limiting-Current Phenomenon by Geometric Field Focusing into Nanopores and Nanoslots. Phys. Rev. E—Stat. Nonlinear, *Soft Matter Phys.* 2010, 81 (4), 1-13. Another approach is to microstructure the surface of the ion selective membrane. Valença et al. demonstrated that the applied potential that is required to start and sustain electroconvection is strongly affected by the geometry of a membrane, indicating that the position and size of vortices can be controlled. Confined Electroconvective Vortices at Structured Ion Exchange Membranes, *Langmuir* 2018, 34 (7), 2455-2463. A reduction in the resistance of approximately 50% was demonstrated when using membranes with structure sizes (100 to 400 μm) close to the dimensions of the mixing layer, resulting in more confined microvortices with less lateral motion in comparison to flat membranes. These smaller and confined vortices can suppress the development of larger instabilities. This behavior can be recognized by a signature alteration to the shape of the CVC.

Accordingly, it is an objective of the disclosure to provide POC microfluidic devices and methods of using the devices that employ electrokinetic enrichment of charged analytes driven by a 3D flow-through electrode incorporating conductive microbeads to achieve stable, high-throughput focusing of charged species coupled to in situ, optical and non-optical (i.e. electrical) sensing at probe-modified beads. It is a further objective of the disclosure to provide POC microfluidic devices and methods of using the devices that employ ion permselective membrane coated microbeads for electrokinetic enrichment. It is still a further objective of the disclosure to provide devices and methods of using the devices that couple the out-of-plane preconcentrator with bioconjugated bead-based assay upstream of the ICP-creating structure for in situ quantification of enriched charged species wherein the charged species are nucleic acids.

Other objects, advantages and features of the present invention will become apparent from the following specification taken in conjunction with the accompanying examples or drawings.

BRIEF SUMMARY OF THE INVENTION

In one aspect, the present disclosure provides a microfluidic device, the device comprising one or more fluidic microchannels wherein the one or more microchannels are connected to at least one inlet and at least one outlet, wherein a background electrolyte solution is infused through at least one inlet, flows through the one or more microchannels, and is withdrawn from at least one outlet. The microchannel(s)

further comprise at least one flow-through 3-dimensional ("3D") flow-through electrode, wherein the 3D electrode comprises an electrode with the addition of conductive microbeads in a bead bed wherein at least a portion of the conductive microbeads is in contact with the electrode and wherein at least a portion of the electrode extends outside of the channel for electrical connection. At least one inlet and at least one outlet are each connected to an electrode, and at least a portion of the conductive microbeads are contained within a primary bead bed which extends at least a portion of the width and length of the microchannel as defined by a bead bed structure within the microchannel. In an aspect, voltage is applied to the inlet and/or outlet electrodes and the 3D electrode for enrichment and separation of charged species at an electric field gradient at the boundary of an ion depleted zone resulting from faradaic processes. The 3D electrode drives charge transfer reactions developing out-of-plane faradaic ion concentration polarization ("fICP") and formation of an ion depleted zone ("IDZ") which allows for counter-flow focusing of charged species. The 3D electrode maintains high efficiency focusing by distributing the IDZ across the microchannel cross section. Additionally, the geometric features of the bead bed increase fluidic stability allowing for higher volumetric throughput.

In another aspect, the present disclosure provides a microfluidic device, the device comprising one or more fluidic microchannels wherein the one or more microchannels are connected to at least one inlet and at least one outlet, wherein a background electrolyte solution is infused through at least one inlet, flows through the one or more microchannels, and is withdrawn from at least one outlet. The microchannel(s) further comprise at least one flow-through 3D flow-through permselective structure, wherein the 3D permselective structure comprises an electrode with the addition of permselective membrane coated microbeads in a bead bed wherein at least a portion of the permselective membrane coated microbeads is in contact with the electrode and wherein at least a portion of the electrode extends outside of the channel for electrical connection. At least one inlet and at least one outlet are each connected to an electrode, and at least a portion of the permselective membrane coated microbeads are contained within a primary bead bed which extends at least a portion of the width and length of the microchannel as defined by a bead bed structure within the microchannel. In an aspect, voltage is applied to the inlet and/or outlet electrodes and the 3D permselective structure for enrichment and separation of charged species at an electric field gradient at the boundary of an IDZ resulting from ion concentration polarization ("ICP"). The steep electric field gradient at the boundary of an IDZ allows for counter-flow focusing of charged species.

In an aspect, the one or more fluidic microchannels have a width of about 0.025 mm to about 20 mm, a height of about 5 μm to about 2000 μm, and a length of about 0.5 mm to about 100 mm.

In an embodiment, the flow-through 3D electrode or 3D permselective structure is placed along the midpoint inside the one or more fluidic microchannels, and/or the flow-through 3D electrode or 3D permselective structure is placed about three-quarters of the distance from at least one of the inlets and at least one of the outlets.

In another embodiment, the device has more than one microchannel wherein the microchannels are connected to the same inlet and the same outlet, or several distinct inlets and several distinct outlets, and wherein each microchannel has at least one flow-through 3D electrode and/or 3D permselective structure, and wherein each flow-through 3D electrode or 3D permselective structure has a separate electrical contact.

In another embodiment, the microchannel further comprises at least one secondary bead bed of microbeads, wherein the microbeads are contained within the secondary bead bed defined by a bead bed structure within the microchannel. In an aspect, the secondary bead bed is located upstream from the flow-through 3D electrode or 3D permselective structure. In an embodiment, the microbeads in the secondary bead bed are not conductive. In another embodiment, the microbeads in the secondary bead bed are bioconjugated. In an aspect, the bioconjugated microbeads comprise biotin binding proteins bound with biotinylated molecules comprising one or more DNA probes.

In an embodiment, microbeads enter the primary bead bed and/or secondary bead bed through auxiliary channel(s) that are sealed prior to device usage.

In an embodiment, the microfluidic device has more than one microchannel and the microchannels are connected to the same inlet and the same outlet, or several distinct inlets and several distinct outlets, and wherein each microchannel has a secondary bead bed each comprised of a different set of microbeads. In an aspect, the microbeads in each secondary bead bed comprise biotinylated molecules comprising DNA probes such that the DNA probes in each secondary bead bed target different nucleic acids.

In an embodiment, the bead bed structure comprises bead bed posts wherein the bead bed posts extend from the floor of the microchannel and are spaced such that the micro beads are contained within the area defined by the bead bed posts. In an aspect, the bead bed posts have a diameter or a cross-section of from about 2 μm to about 500 μm, and the gaps between the bead bed posts are from about 1 μm to about 250 μm. In another aspect, the bead bed structure comprises a weir structure, a porous matrix, a chemical linker, or combination thereof.

In an embodiment, the bead bed extends the length of the microchannel from about 0.025 mm to about 5 mm.

In another embodiment, the device further comprises a power source connected with the inlet electrode and/or the outlet electrode and/or the 3D electrode and/or the 3D permselective structure, wherein the power source is configured to supply a voltage in the range of from about 1 V to about 500 V. In an aspect, the power source is a battery.

In an embodiment, the 3D electrode and/or the 3D permselective structure comprises a planar microband electrode. In an aspect, the planar microband electrode extends the length of the microchannel from about 0.005 mm to about 5 mm, and is from about 0.05 μm to about 1 μm thick. In another aspect, the 3D electrode and/or the 3D permselective structure comprises a rod, a wire, a pin, or combinations thereof. In another aspect, the rod, wire, and/or pin has a diameter of from about 0.05 mm to about 2 mm. In an embodiment the 3D electrode and/or the 3D permselective structure comprises a conductive epoxy, an ionic liquid, or combinations thereof.

In an aspect, the microbeads in the 3D electrode and/or 3D permselective structure have a diameter of from about 1 μm to about 500 μm, preferably from about 10 μm to about 20 μm.

In an embodiment, the 3D electrode comprises a planar microband electrode comprised of Au and microbeads comprised of Ag. In another embodiment, the permselective membrane coated microbeads in the 3D permselective structure are coated with an ion permselective membrane.

In an aspect, the diameter of the microbeads in the secondary bead bed is from about 1 μm to about 500 μm.

In an embodiment, the microbeads in the secondary bead bed comprise polystyrene carboxylate and have a diameter of from about 10 μm to about 16 μm.

In another embodiment, the background electrolyte solution comprises a buffer. In an aspect, the background electrolyte solution comprises a biological sample.

The present disclosure provides for a method of focusing at least one charged species from a background electrolyte solution comprising flowing the background electrolyte solution containing targeted charged species through the microchannel(s) of the microfluidic device in any combination of any embodiments or aspects or descriptions herein, applying a voltage to the electrodes at the inlet and/or outlet of the device and/or the 3D electrode and/or the 3D permselective structure for a period of time so the targeted charged species is focused along the electric field gradient at the boundary of an ion depleted zone created by the 3D electrode or 3D permselective structure.

In another embodiment, the present disclosure provides for a method of focusing at least one charged species from a background electrolyte solution comprising flowing the background electrolyte solution containing targeted charged species through the microchannel(s) of the microfluidic device in any combination of any embodiments or aspects or descriptions of the device disclosed herein, applying a voltage to the electrodes at the inlet and/or outlet of the device and/or the 3D electrode and/or the 3D permselective structure for a period of time so the targeted charged species is focused at the strong electric field at the edge of an ion depleted zone created by the 3D electrode or 3D permselective structure so the targeted charged species is focused within the secondary bead bed.

In an embodiment, the method further comprises optical detection of the at least one targeted charged species at the ion depleted zone. In an aspect, the optical detection is obtained by fluorescence imaging, colorimetry, infrared absorption spectroscopy, ultraviolet absorption spectroscopy, radiometric imaging, Raman spectroscopy, or combinations thereof.

In an embodiment, the method further comprises non-optical detection of the at least one targeted charged species at the ion depleted zone. In an aspect, the non-optical detection of enrichment of a targeted charged species is obtained by a change in impedance. In an aspect, the change in impedance is observed by a shift in slope in the overlimiting region of a current voltage curve at the 3D electrode and/or the 3D permselective structure. In another aspect, the change in impedance is observed by a shift in absolute current at a given voltage at the 3D electrode and/or the 3D permselective structure. In another aspect, the change in impedance is observed by electrochemical impedance spectroscopy at a voltage in the overlimiting region of the 3D electrode and/or the 3D permselective structure.

In an embodiment, the targeted charged species is a nucleic acid, protein, antigen, antibody, bioparticle, bacteria, virus, other biomolecule, or combinations thereof.

In an embodiment, the background electrolyte solution has a linear flow velocity from about 0 mL min$^{-1}$ to about 1 mL min$^{-1}$.

In an embodiment, the method occurs at point-of-care. In an aspect, the method occurs at point-of-care, and the background electrolyte solution is a biological sample.

In an aspect, the electrode at the outlet is set at 0 V, the electrode at the inlet is set from about 250 mV to about 500 V, and the applied voltage at the 3D electrode is set such that a sufficient fraction of the current at the inlet is redirected to the outlet to avoid overly high current density at the 3D electrode.

In an aspect, the throughput is from about 0.001 mL/hour to about 60 mL/h.

In another aspect, the enrichment of a targeted charged species is at least about 300-fold in about 60 minutes.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a schematic representation of an embodiment of the device design, near the center of a channel.

FIG. 2A is an illustration of the mechanisms of ion concentration polarization.

FIG. 2B is an illustration of the mechanisms of faradaic ion concentration polarization.

Figure 3:
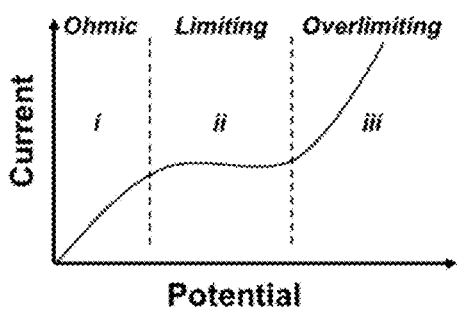
FIG. 3 is an exemplary representation of a current-voltage curve displaying characteristic ohmic (i), limiting (ii), and overlimiting (iii) regions.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to high-throughput microfluidic devices comprising one or more microchannels each which comprise a three-dimensional ("3D") electrode comprising electrically conductive microbeads, alternatively ion conductive permselective membrane coated microbeads, and an optional secondary bead bed. In an embodiment, the secondary bead bed is located upstream of the 3D electrode. The present disclosure further relates to methods of using the devices to electrokinetically focus a charged species. In an embodiment, the charged species is focused within the secondary bead bed. The present disclosure further relates to point-of-care ("POC") use of the devices and in situ quantification of electrokinetically enriched species, such as nucleic acids, by both optical and non-optical detection.

The embodiments described herein are not limited to any particular device or method of using the device, which can vary and are understood by skilled artisans based on the present disclosure herein. It is further to be understood that all terminology used herein is for the purpose of describing particular embodiments only, and is not intended to be limiting in any manner or scope. For example, as used in this specification and the appended claims, the singular forms "a," "an," and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

The term "about," as used herein, refers to variations in size, distance or any other types of measurements that can be resulted from inherent heterogeneous nature of the measured objects and imprecise nature of the measurements itself. The term "about" also encompasses variation in the numerical quantity that can occur, for example, through typical measuring or handling procedures in the real world; through inadvertent error in these procedures; through differences in the manufacture, source, or purity of the ingredients used to make the device or carry out the methods, and the like. Whether or not modified by the term "about", the claims include equivalents to the quantities.

Microfluidic Devices

In one aspect, the present disclosure provides a microfluidic device. The device comprises an inlet and an outlet, both in fluid connection with at least one microchannel. The one or more fluidic microchannels are configured to retain and move a background electrolyte ("BGE") solution from inlet to outlet. In another aspect, the present disclosure provides a microfluidic device comprising at least one flow-through 3D electrode in the microchannel. The at least one microchannel comprises a conductive electrode wherein the electrode extends across at least a portion of the channel with a portion outside of the channel for connection to a wire lead. In an embodiment, the electrode is a planar microband. In another embodiment, the electrode is a conductive rod or wire. In yet another embodiment, the electrode is a conductive epoxy or ionic liquid that fills or partially fills the auxiliary channel inlet.

In an embodiment, the microchannel further comprises a bead bed wherein conductive microbeads are packed with at least a portion of the microbeads in contact with the electrode to create a 3D electrode. The bead bed comprises a structure in which to define the size of the bead bed and to contain the beads. The structure can be anything as known in the art to define the bead bed area and retain the beads in the bead bed while maintaining flow of the BGE solution through the microchannel. In an embodiment, the structure comprises bead bed posts which extend from the floor of the microchannel and are spaced such that the microbeads are contained within the area defined by the bead bed posts. In another embodiment, the structure is a weir structure. In yet another embodiment, the structure is a porous matrix. In yet another embodiment, the microbeads are bound together by a chemical linker. The bead bed further comprises an auxiliary bead bed channel in which to introduce the microbeads into the bead bed.

The BGE solution is infused in the inlet, flows from the inlet through the 3D electrode, and is withdrawn from the outlet.

In an embodiment, permselective membrane coated microbeads are packed into the bead bed with at least a portion of the microbeads in contact with an electrode comprising a 3D permselective structure. The BGE solution is infused in the inlet, flows from the inlet through the 3D permselective structure, and is withdrawn from the outlet.

In an embodiment, the microchannel further comprises at least one secondary bead bed, wherein microbeads are packed, in the microchannel. In an embodiment, the secondary bead bed is placed closer to the inlet than the 3D electrode ("upstream"). This at least one secondary bead bed comprises a structure defining the size of the bead bed and containing the beads. The structure can be anything as known in the art to define the bead bed area and retain the beads in the bead bed while maintaining flow of the BGE solution through the microchannel. In an embodiment, the structure comprises bead bed posts which extend from the floor of the microchannel and are spaced such that the microbeads are contained within the area defined by the bead bed posts. In another embodiment, the structure is a weir structure. In yet another embodiment, the structure is a porous matrix. In yet another embodiment, the microbeads are bound together by a chemical linker. The bead bed further comprises an auxiliary bead bed channel in which to introduce the microbeads into the bead bed. In a further embodiment, the device comprises one or more secondary bead beds closer to the outlet than the 3D electrode ("downstream"). The BGE solution is infused in the inlet, flows from the inlet through the 3D electrode or permselective structure and any secondary bead beds, and is withdrawn from the outlet.

In an embodiment, at least one microchannel comprises more than one 3D electrode and/or more than one 3D permselective structure. In another embodiment, at least one microchannel comprises more than one 3D electrode and/or more than one 3D permselective structure each of which further comprises at least one secondary bead bed. In another embodiment, at least one microchannel comprises more than one 3D electrode and/or more than one 3D permselective structure each of which further comprises at least one secondary bead bed, and each in series from inlet to outlet through the microchannel. In an aspect, more than one 3D structure in series in a single microchannel allows for enrichment of a mixture of analytes successively in distinct bioconjugated bead beds. In another aspect, more than one 3D structure in series in a single microchannel allows for movement of an enriched plug down a channel in a controlled manner. In another aspect, more than one 3D structure in series in a single microchannel allows for enrichment in channels with increasingly small cross section for higher degrees of enrichment.

In an embodiment, more than one, or several, microchannels are in fluid connection to a singular inlet and a singular outlet, wherein each microchannel comprises a flow-through 3D electrode, alternately a 3D permselective structure, and a secondary bead bed, wherein each secondary bead bed comprises a unique set of microbeads. In another embodiment, more than one, or several, microchannels are in fluid connection to a singular inlet and more than one outlet. In another embodiment, more than one or several microchannels are in fluid connection to a singular inlet and each microchannel has a unique outlet. In an embodiment, each microchannel has more than one inlet, wherein at least one inlet is connected to an electrode. In another embodiment, each microchannel comprises at least one secondary bead bed wherein the at least one secondary bead bed is configured to bind with a specific biotinylated molecule as a bead-based assay. A BGE solution is infused into the inlet and simultaneously directed through the microchannels wherein the BGE solution is subjected to different bead-based assays in each channel before being withdrawn from the outlet or outlets. The flow-through 3D electrode in any one microchannel may be comprised of the same electrode materials as another 3D electrode in a different microchannel, or may comprise different materials. The 3D permselective structure in any one of the microchannels may comprises the same permselective membrane coated microbeads as another 3D permselective structure in another channel or may comprise different materials. In an embodiment, each microchannel may comprise one or more, or several, 3D electrode and/or 3D permselective structures, and each 3D electrode or 3D permselective structure may further comprise at least one secondary bead bed. The flow-through 3D electrode, or 3D permselective structure of each microchannel has its own electrical connection for measurements, for example current-voltage curves.

In an embodiment, a number of microchannels can be grouped together and then connected fluidly with another group(s) of microchannels. Within each group of microchannels, any two microchannels can be parallel to each other, on top of each other, or in another arrangement.

An exemplary device is illustrated in FIG. 1. This figure illustrates a midpoint of a microchannel (labeled "Main channel") and a planar microband electrode. The channel segments leading to the inlet and outlet are not depicted. The auxiliary channels are employed to pack the beads into the bed channel. The voltage bias is applied between the electrodes at the inlet and outlet, indicated by "+". The wire lead connected to the planar electrode is indicated by "−". A BGE solution is infused into an inlet at left and withdrawn from an outlet at right as indicated by the arrows indicating infuse flow and withdraw flow. The inlet and outlet each comprise an electrode. Microbeads comprised of conductive or semi-conductive materials are packed into the primary or conductive bead bed via the auxiliary bead bed channel overlying the planar electrode to create the flow-through 3D electrode. Alternatively, in an embodiment microbeads coated with a permselective membrane are packed into the primary bead bed via the auxiliary bead bed channel to create the flow-through 3D permselective structure. In embodiments with a secondary bead bed, microbeads are packed into the secondary bead bed via the connected auxiliary bead bed channel. Auxiliary bead bed channels are sealed prior to device usage. In an embodiment the secondary microbeads are employed as a bead bed assay. In an embodiment, the secondary microbeads are bioconjugated to bind with biotinylated molecules.

As used herein, a microchannel is referred to as a passageway from an inlet to an outlet wherein the BGE solution flows from inlet to outlet. The width of a microchannel is referred to as the horizontal distance of the two points that are on the opposite edges of the cross-section perpendicular to the intended fluidic flow and are furthest away from each other. As used herein, the length of a microchannel is referred to as the distance from the inlet to the outlet through the microchannel along the intended fluid flow. As used herein, the height of the microchannel is referred to as the vertical distance from the floor of the microchannel to the ceiling of the same.

As used herein, a microchannel is referred to as having a width of from about 0.025 mm to about 20 mm, and with a length of from about 0.5 mm to about 100 mm, and a height from about 5 μm to about 10,000 μm tall. The cross section of a microchannel in principle can have any two-dimensional shape, such as square, rectangular, circle, or a combination thereof. A microchannel may be straight or curved. In an embodiment, the channel comprises pillars for support. The pillars extend from the floor of the microchannel to the ceiling of the microchannel. The pillars may be of any shape, such as a round pillar. The size of the pillar is selected as to support the micro channel while not inhibiting the flow-through property of the device.

As used herein, a bead bed is an area defined by a structure in the microchannel wherein microbeads are packed. In an embodiment, the bead bed area extends into a portion of the channel, and in some embodiments spans the entire width of the channel. In an embodiment, the bead bed area spans a portion of the length of the microchannel, from about 0.025 mm to about 5 mm. In an aspect, the structure defining the area of the bead bend comprises bead bed posts. The bead bed posts are spaced such as to retain the beads in the bead bed while maintaining flow of the BGE solution through the microchannel. The bead bed posts have a size, cross-section, and/or diameter of from about 2 μm to about 500 μm. The gaps between the posts are from about 1 μm to about 250 μm. The bead bed posts extend up from the floor of the microchannel and may extend to the ceiling of the microchannel and may be of any shape, such as round pillar or post or a rectangular pillar or post. As used herein, an auxiliary channel is the channel used for packing the microbeads into the bead beds. Auxiliary channels may be from about 0.01 to about 1 mm wide, and from about 0.05 to about 5 mm long. In an embodiment, the microbeads enter the bead bed through an auxiliary channel that is sealed prior to device usage. In another embodiment the electrode contacts the microbeads via the auxiliary channel.

In some other embodiments, the microfluidic devices disclosed herein have 1, 2, 3, 4 or many more microchannels wherein each microchannel is in fluid connection with a singular inlet and outlet. In another embodiment, the microchannels are in fluid connection to a singular inlet and more than one outlet. In another embodiment, more than one or several microchannels are in fluid connection to a singular inlet and each microchannel has a unique outlet. In an embodiment, each microchannel has more than one inlet, wherein at least one inlet is connected to an electrode. In an embodiment, each channel is configured as an assay for a particular analyte and with its own electrical contact.

In some embodiments, the microfluidic device further comprises a power source that is configured to have electrical communication with the electrodes at the inlet and outlet, and have electrical communication with the 3D electrode and/or the 3D permselective structure. The power source is configured to supply DC with a voltage range from about 1 V to about 500 V and any value in between. In an embodiment, the power supply is a battery.

In an aspect, the inlet and outlet are in electrical contact with an electrode. Any electrode known in the art is acceptable, for example the electrode may comprise a planar electrode such as a thin metal film, pins and/or rods, wires, and the like. In an embodiment, the electrodes at the inlet and outlet comprise stainless steel tubing wherein the stainless steel tubing connects the inlet and outlet, each, with tubing sufficient to transport the BGE solution through the microchannel from inlet to outlet. In an embodiment, the tubing connected to the inlet and outlet electrodes comprises PTFE.

Any method known in the art sufficient to transport the BGE solution through the at least one microchannel from inlet to outlet is acceptable for this device. In an embodiment, the inlet and outlet are configured such that there is uniform flow of the BGE through the at least one microchannel. As known in the art, there are various ways to ensure uniform flow, any one of which is acceptable. In an embodiment in the inlet and outlet are open reservoirs wherein uniform flow is gravity-driven, for instance by a fluid height differential, or a larger volume of fluid in the inlet than outlet, or by tilting the device such that the inlet is located in a higher plane than the outlet. In another embodiment, the inlet and outlet comprise tubing for fluid distribution. In an embodiment, fluid flow is ensured by a pump, or other device like a syringe. In an embodiment, the inlet serves as a port for a larger receptacle to plug into the inlet. In another embodiment, the outlet comprises a cotton plug, paper, a field of pillars, or other material or media to drive capillary flow through the device. In another embodiment, the inlet further comprises a filter to remove particulate matter such as debris or biological cells. In another embodiment the outlet comprises a receptacle to accept the BGE and or any other waste material.

In some embodiments, the walls, floor, and/or ceiling of the microchannels comprise a polymeric material. In some embodiments, the walls, floor, and/or ceiling of the microfluidic channels comprise polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass or the like. In an embodiment, the walls, floor, and/or ceiling of the microchannels comprise the resin of a 3D printer. In an embodiment, the walls, floor, and/or ceiling of the microchannels comprise polyethylene glycol. In another embodiment, the walls of the microchannel comprise crosslinked polyethylene glycol diacrylate ("PEGDA") resin. In an embodiment, the walls, floor, and/or ceiling of the microchannel require a surface coating to prevent analyte from adsorbing on the walls, floor, and/or ceiling. As used herein, a surface coating comprises surfactant or bovine serum albumin or other substance known in the art to prevent analyte adsorption due to hydrophobic microchannel material.

Ion Concentration Polarization

Ion concentration polarization ("ICP") is the simultaneous enrichment and depletion of ions at opposing ends of an ion permselective structure under a voltage bias. The steep electric field gradient at the boundary of a created ion depleted zone ("IDZ") may then be leveraged for counter-flow focusing of charged species. An ion permselective structure is one that transports certain ions while blocking ions of opposite charges. The mechanism of ICP is illustrated in FIG. 2A, with a cation permselective membrane.

Faradaic ion concentration polarization ("fICP") differs from conventional ICP in that the IDZ is created by an electrode and formed as a result of faradaic processes at the electrode surface. In an embodiment, fICP proceeds via base neutralization of buffer ions comprising the BGE solution. In an embodiment, the faradaic reaction at the electrode generates $OH^-$ which can neutralize cations present in the BGE resulting in uncharged species. The localized loss of charge-carrying ions results in the formation of an IDZ. Charged analytes will then be concentrated at the IDZ boundary by the same principles operative in conventional ICP. This is illustrated in FIG. 2B. This fICP process resembles the transport of cations from the anodic to cathodic microchannel compartments through a cation permselective membrane. In the present disclosure, ion depletion is carried out at a single pole, a cathodic electrode, located within a microchannel. An advantage of fICP is that charge transfer resistance, instead of the ionic resistance of a membrane, dictates the required potential bias and is often lower, allowing a smaller power supply, or batteries, to be used.

Figure 4A:
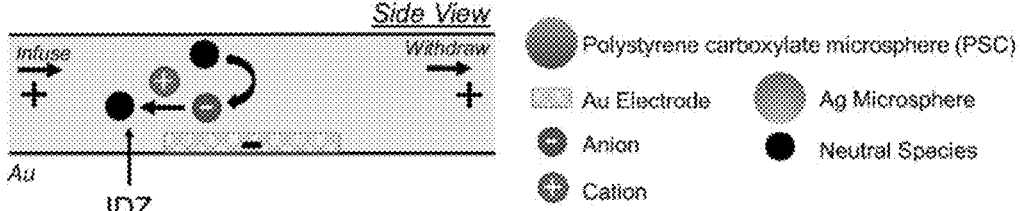
FIG. 4A depicts an illustrated side view of a faradaic ion concentration polarization device design and operation with a planar Au microband electrode.
Figure 4B:
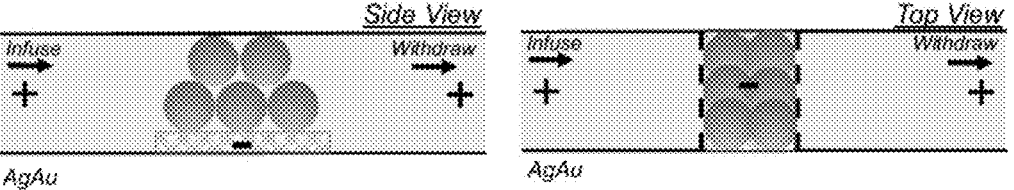
FIG. 4B depicts an illustrated side view and top-down view of a faradaic ion concentration polarization device design and operation with a 3D electrode that is a planar Au microband and Ag microbeads.

The present disclosure relates to out-of-plane fICP in which electrokinetic focusing of charged species is driven by a 3D electrode comprising a planar microband electrode further comprising conductive microbeads. fICP using a planar microband to facilitate electrochemical reactions, as illustrated in FIG. 4A, generates an IDZ that may not extend the full height of a microchannel. Therefore, a fraction of the analyte escapes, carried over the IDZ by convection, thereby decreasing the efficiency of focusing. The present disclosure employs a flow-through 3D electrode wherein conductive microbeads are overlying the planar electrode to facilitate creation of an IDZ that extends the height of the microchannel. This system is illustrated in FIG. 4B.

The present disclosure further relates to out-of-plane ICP in which focusing of charged species is driven by permselective membrane coated microbeads overlying a planar microband electrode. Voltage is applied to the microband and the permselective membrane pulls cations through the membrane generating an IDZ analogous to the 3D electrode described in the preceding paragraph.

3D Electrode and 3D Permselective Structure

As used herein, an electrode is referred to as a piece of conductive or semi-conductive material, or combination thereof. As used herein, a conductive material is one that allows the flow of charge in one or more directions. Metals are common conductors. As used herein, a semi-conductive material is one that is not as conductive as a conductor, but is more conductive than an insulator. The conductivity of semi-conductive material can be increased and controlled by doping techniques as known in the art.

The electrode of the present invention may be any conductor or semiconductor as known in the art, as long as the electrode extends within, or is in contact with, at least a portion of the at least one microchannel with a portion of the electrode outside of the channel for electrical connection. In an embodiment, the electrode is in contact with at least a portion of the conductive and/or permselective membrane coated microbeads. In an embodiment, the electrode is a planar microband. In another embodiment, the electrode is a conductive rod or wire. In yet another embodiment, the electrode is a metal epoxy that fills or partially fills the auxiliary channel inlet.

In an embodiment, the electrode is a planar microband electrode from about 0.005 mm to about 5 mm wide and long enough such that at least a portion of the electrode is within the channel and at least a portion extends outside of the microchannel to make electrical contact to a wire lead. The thickness of the microband is from about 0.05 $\mu$m to about 1 $\mu$m, sufficient to allow space for microbeads to create a 3D flow-through electrode. In an embodiment, the planar microband has a thickness of 0.1 $\mu$m. In another embodiment, the electrode is a rod and/or wire with a diameter of from about 0.05 mm to about 2 mm and long enough such that at least a portion of the electrode is within the channel and at least a portion extends outside of the microchannel to make electrical contact to a wire lead. In an embodiment, the electrode extends outside of the microchannel though a side port. In yet another embodiment, the rod and/or wire is inserted to at least a portion of the conductive and/or permselective membrane coated microbeads through the auxiliary channel. In another embodiment, the electrode is a conductive epoxy is used to seal the auxiliary channel with at least a portion of the conductive epoxy in contact with at least a portion of the conductive and/or permselective coated microbeads and then the epoxy connected to a conductive rod and/or wire for electrical connection. In another embodiment, the electrode is a conductive material patterned onto or incorporated into the walls, floors, and/or ceiling of the microchannel. This electrode may comprise a conductive polymer such as polyaniline, polythiophene, or poly(3,4-ethylenedioxythiophene) ("PEDOT"), an ionic liquid, a plastic doped with conductive particles or nanotubes such as carbon-doped PDMS, or an ionically conductive solid phase such as a metal organic framework.

According to the invention, the electrode and/or the microbeads, alone or in part, or together, drive faradaic reactions and/or ion permselection such as to neutralize or remove, respectively, the charged species in a BGE solution. The material of the electrode can be selected such as to neutralize charged species in a BGE solution creating an IDZ to focus charged species, as known to those skilled in the art. The electrode comprises an electric conductor, semiconductor, or a combination thereof. The electrode may comprise, but is not limited to, elemental gold (Au), silver (Ag), and/or platinum (Pt), alloys such as stainless steel or titanium/tungsten (Ti/W), copper, nickel, glassy carbon, pyrolyzed photoresist, silver/silver chloride (Ag/AgCl). In another embodiment, the electrode comprises semi-conductive material, boron-doped diamond, or n-doped or p-doped silicon, or a combination thereof. In an embodiment, and without being limited to a particular theory, the electrode is comprised of a material that will reduce water to produce OH$^-$ to neutralize charged species in a BGE solution creating an IDZ to focus charged species. In a preferred embodiment, the planar microband is made of gold (Au). In another embodiment, the electrode is Ag/AgCl which, without being limited to a particular theory, undergoes Ag+ reduction, or oxidation if acting as an anode, which then transmits current to and from the microbeads and the BGE without oxidation or reduction of water therefore yielding no gaseous products.

As used herein, a 3D electrode refers to an electrode as previously described in electrical contact with a packed bed of microbeads. Electrically conductive microbeads together with the electrode comprise the 3D electrode. A BGE flows through the bead bed creating a flow-through 3D electrode. As used, herein, the microbeads have a surface comprised of conductive or semi-conductive material or a combination thereof. The material of the microbeads of the 3D electrode can be selected such as to neutralize charged species in a BGE solution creating an IDZ to focus charged species, as known to those skilled in the art. In an embodiment, the microbeads of the 3D electrode are made of a material that facilitate electrochemical reduction of water to produce OH$^-$ to neutralize charged species in a BGE creating an IDZ to focus charged species.

In some embodiments, the microbeads of the 3D electrode comprise elemental metal, gold (Au), silver (Ag), nickel (Ni), iron (Fe), carbon (C), platinum (Pt), a conductive polymer, an insulator coated with a conductor, a magnetic bead with a conductive coating, and/or combinations thereof. In another embodiment, the microbeads of the 3D electrode comprise semi-conductive material, boron-doped diamond, or n-doped or p-doped silicon, or a combination thereof. In an embodiment, the microbeads are comprised of gold (Au), silver (Ag), and/or platinum (Pt), or a combination thereof. In a preferred embodiment, the microbeads are comprised of Ag. In an embodiment the microbeads are selected such that the potential to reduce water to OH$^-$ is the same as the planar microband. In a preferred embodiment the 3D electrode is comprised of Au planar microband electrode and Ag microbeads.

The microbeads must be of a size and density that allows flow through of a BGE. In an embodiment, the diameter of the microbeads is from about 1 $\mu$m to about 500 $\mu$m. In a preferred embodiment the microbeads are Ag with a diameter of from about 10 $\mu$m to about 20 $\mu$m.

The 3D electrode as described herein is illustrated in FIG. 4B. FIG. 4B shows a side view and a top view of Ag microbeads overlying a planar Au microband. Also indicated in this figure is the flow through nature of the BGE through the 3D electrode.

In an embodiment, the conductive microbeads and an electrode are not in direct contact. In this embodiment, a voltage is applied between the inlet and the outlet, or between the inlet and an electrode adjacent to the bead bed. In this embodiment, the conductive bead bed polarizes to become a bipolar electrode such that one end acts as an anode and the other end acts as a cathode.

In another embodiment ionically conductive permselective membrane coated microbeads in contact with the electrode comprise a 3D permselective structure. In an embodiment, the microbeads are comprised of spheres coated with a cation permselective membrane. As used herein, the permselective membrane material is selected such that cations are transported through the bead bed to the electrode, while anions of the BGE are excluded creating an IDZ. In an alternative embodiment, the microbeads are comprised of spheres coated with an anion permselective membrane. Anions are transported through the bead bed to the electrode, while cations of the BPE are excluded creating an IDZ. The material is selected specific to the charge of the targeted species. For an anionic analyte, cation permselective membrane coated microspheres in electrical contact with a cathodic electrode will lead to the formation of an IDZ that facilitates electrokinetic stacking of the analyte. For a cationic analyte, anion permselective membrane coated microspheres in electrical contact with an anodic electrode will lead to the formation of an IDZ that facilitates electrokinetic stacking of the analyte. The electrode accepts ions from the bead bed, removing them from the electrolyte by faradaic reactions, storage in the electrical double layer at the electrode surface, their transport into another ionically conductive phase, or a combination of these processes. In some embodiments, the membrane coated microspheres comprise polystyrene, latex, metallic, magnetic, carbon, glass, or composite spheres with a diameter from about 1 μm to about 500 μm and having an outer layer or coating with charged chemical moieties (e.g., sulfonate, carboxylate, or quaternary amine groups) positioned on its surface or within nanopores such that counter-ions (ions of opposite charge to the chemical moieties) are permitted while co-ions are excluded (Donnan exclusion). In a preferred embodiment, the coating is an ionophore such as Nafion™ distributed by The Chemours Company.

In an embodiment, the membrane-coated microbeads and an electrode are not in direct contact. In this embodiment, a voltage is applied between the inlet and the outlet, or between the inlet and an electrode adjacent to the bead bed. In this embodiment, the membrane-coated bead bed polarizes so that electrolyte ions are depleted at one end and enriched at the opposing end.

As used herein, the 3D electrode or 3D permselective structure may be placed in any location within the microchannel. In an embodiment, the 3D electrode or 3D permselective structure is at the midpoint of the channel. In a preferred embodiment, the 3D electrode or 3D permselective structure is three quarters of the distance from the inlet to the outlet.

Secondary Bead Bed

As used herein, a secondary bead bed is a section of the microchannel wherein microbeads are packed and wherein the enriched analytes are focused along the boundary of the created IDZ of the above described 3D electrode or 3D permselective structure. In an aspect, a secondary bead bed stabilizes naturally occurring vortical fluid flow within the IDZ and facilitates surface conduction of ions to the electrode. In an embodiment, the secondary bead bed is either upstream or downstream of the 3D electrode or 3D permselective structure. In an embodiment, the microchannel comprises a secondary bead bed upstream and another secondary bead bed downstream of the 3D electrode or 3D permselective structure. In a preferred embodiment, the secondary bead bed is upstream of the 3D electrode or 3D permselective structure. In an aspect, the geometry of the secondary bead bed helps mitigate fluid instability that leads to unwanted mixing, as evidenced by smaller vortices with smaller radius of curvature in the IDZ boundary. In an aspect, the secondary bead bed geometrically confines the BGE solution and enhances surface conduction of ions from the bulk solution to the electrode.

In an aspect, the material of the microbeads of the secondary bead bed is selected such that the material is not conductive. In an embodiment, the microbeads are comprised of polystyrene carboxylate ("PSC"). In another aspect, microbeads of the secondary bead bed comprise conductive or semi-conductive material, and not in electrical contact with an electrode. In another aspect, the microbeads of the secondary bead bed comprise magnetic material. In a preferred embodiment the microbeads are bioconjugated. As used herein bioconjugated beads comprise biotin-binding proteins to bind with biotinylated molecules. In an embodiment, the bioconjugated beads comprise one or more DNA probes. As used herein biotinylated molecules are biomolecules that have been modified with biotin and selected for the ability to attach to, bind to, or hybridize to, a specific analyte such as a protein, nucleic acid, or other molecule. In an embodiment, the biotinylated molecules comprise antibodies, peptides, ligands, toxins, oligonucleotides, and/or DNA probes. As used herein, a DNA probe can be any DNA probe as known in the art. In an embodiment, a DNA probe may comprise antibodies, aptamers, nucleic acids, xeno nucleic acids (XNA), peptide nucleic acids (PNA), morpholino nucleic acids, threose nucleic acids (TNA), and the like, and combinations thereof. In an embodiment, the microbeads are coated with streptavidin protein, wherein the streptavidin is a linker to attach the desired probe, such as a biotinylated-DNA probe used to detect a targeted nucleic acid. In an embodiment the streptavidin coated microbeads further comprise a probe with a fluorescent label to enable optical detection of the targeted nucleic acid.

In an embodiment, the microbead material is selected such that the microbead itself does not carry much charge and is therefore more sensitive to certain charged species, furthermore, the charge of the microbeads may be modified to be positive or neutral depending on the desired sensitivity to a specific charged species. For example, and without being limited to a specific theory, bioconjugated beads facilitate ion transport to the conductive bead bed and the ability to conduct ions depends on the surface charge of the microbeads, which may be dependent upon the number density of charged chemical moieties or molecules on the bead surface. The biorecognition event leads to a change in surface charge. Therefore, the number density of unbound microbead and biorecognition sites is important for sensitivity.

As used herein, an analyte is a charged species that is targeted for focusing. In a preferred embodiment, the analyte comprises proteins, antigens, antibodies, bioparticles, bacteria, virus, nucleic acids, or other biomolecules or combination thereof. As used herein, biomolecules comprise DNA, RNA, aptamers, antibodies, peptides, peptide nucleic acids, morpholino oligonucleotides, receptors, a small molecule that binds a cell-surface receptor such as folic acid, and the like, and combinations thereof. As used herein, a bead-based assay is a secondary bead bed as described herein wherein the analyte is focused. In an embodiment the microbeads of the secondary bead bed are selected as an assay for a specific analyte.

Figure 23:
FIG. 23 is a schematic representation of the configuration employed for the assay for the BRAF-Mut sequence (SEQ ID NOs: 1-3).

As an exemplary illustration, FIG. 23 shows an example of a streptavidin-coated polystyrene ("PS") microbead modified with a biotinylated oligonucleotide probe ("1° probe"). The sequence of this probe was designed to be complementary to the 5' end of the V600E BRAF mutant ("BRAF-Mut") gene, which has a high prevalence in melanoma (about 45% of patients). A secondary probe ("2° probe"), complementary to the 3' end of the BRAF-Mut gene, and tagged with fluorescein ("FL"), was included to aid in fluorescence-based detection. The targeted gene encodes the BRAF enzyme, which participates in a signaling pathway responsible for cell growth. The V600E mutation leads to increased activity of the BRAF enzyme, and ultimately causes uncontrolled growth and spread of tumor cells. The detection of this mutation in tumor tissue or as circulating tumor DNA ("ctDNA") in blood plasma has diagnostic value and is a pharmacodynamic indicator for treatment with drugs that inhibit BRAF enzyme. A secondary bead bed packed with microbeads such as the PSC microbead modified with biotinylated oligonucleotide probe designed to be complementary to the 5' end of the BRAF-Mut gene would create a BRAF-Mut assay, and the BRAT-Mut gene the analyte. This BRAF-Mut assay system is an illustrative example and the assay can be configured to select for any analyte by modifying the biotinylated probe to select for the particular analyte.

An advantage of the present disclosure is the POC detection of such analytes through such methods as described herein.

As used herein, the microbeads of the secondary bead bed must be of size and shape such that allows flow-through of the BGE solution. In an embodiment, the diameter of the microbeads is from about 1 μm to about 500 μm. In a preferred embodiment the microbeads are comprised of PSC with a diameter of from about 10 μm to about 16 μm.

Figure 4C:
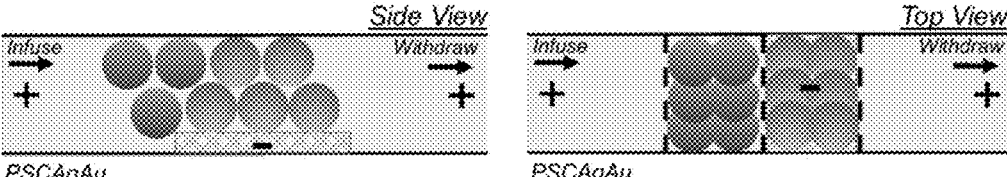
FIG. 4C depicts an illustrated side view and top-down view of a faradaic ion concentration polarization device design and operation with a 3D electrode that is a planar Au microband and Ag microbeads and a secondary polystyrene carboxylate bead bed upstream of the 3D electrode.

The device incorporating a secondary bead bed as described herein is illustrated in FIG. 4C. This figure depicts a side view and a top view of a midpoint in a microchannel with a flow-through 3D electrode ("AgAu") and an upstream secondary bead bed with PSC microbeads ("PSCAgAu").

Figure 24:
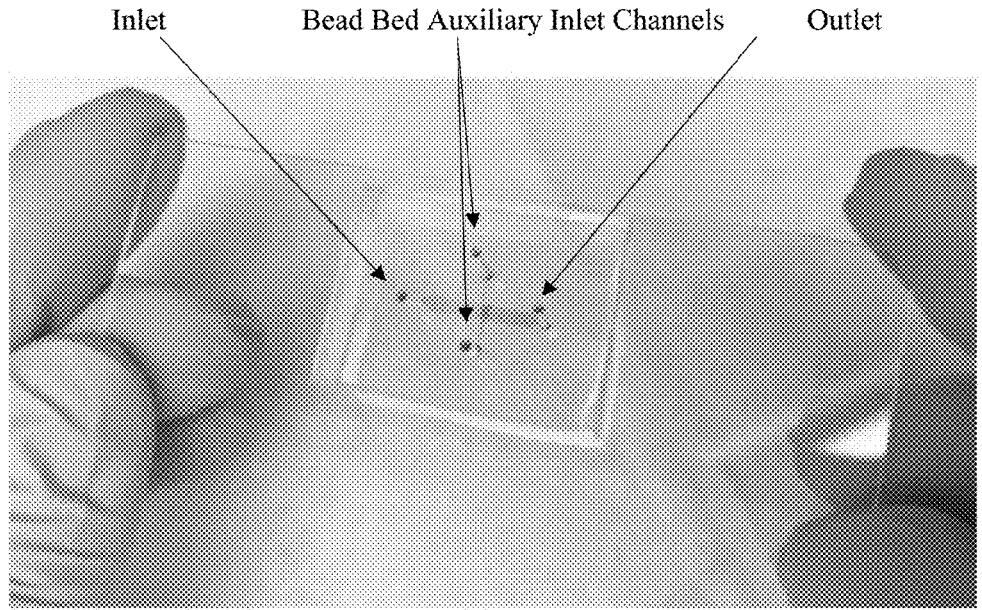
FIG. 24 shows a photograph of an example of the device according to the invention, but without the electrodes at the inlet and outlet and without the contact to the planar electrode.
Figure 25:
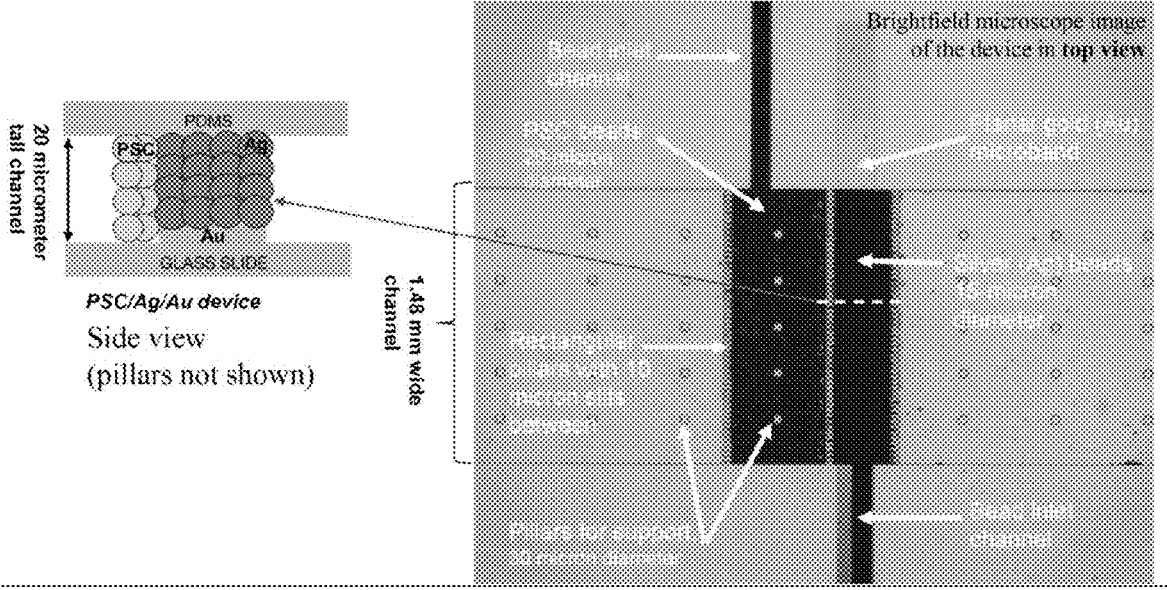
FIG. 25 is a brightfield microscope image of the device in top view, coupled with a cross-section of the 3D flow-through electrode and upstream secondary bead bed.

Dimensions for two exemplary device designs that incorporate a flow-through 3D electrode and an upstream secondary bead bed are summarized in Table 1, in the Examples section. A device according to the dimensions of Device Design 1 in Table 1 is shown in a photograph in FIG. 24, however this device is for illustrative purposes and is missing tubing with electrodes at the inlet and outlet and the contact to planar electrode. To operate the device, the auxiliary channels to the bead beds are sealed, and tubing is inserted into the inlet and outlet. In an embodiment, the tubing is conductive for electrical contact. In a preferred embodiment the tubing is stainless steel. A brightfield microscope image of the device in top view is shown in FIG. 25.

Background Electrolyte Solution

As used here, a BGE solution is an aqueous solution wherein the solution contains dissolved ions. As used here, a BGE comprises an ionically conductive liquid. In an embodiment, the BGE comprises a buffer. As used herein, a buffer is a solution that resists a shift in pH that would otherwise be caused by addition of an acid or base. This disclosure is meant to incorporate any buffer commonly known to the skilled artisan. In an embodiment, the BGE comprises $KNO_3$, phosphate buffer, Tris buffer, and combinations thereof. In an embodiment, the BGE comprises $Tris.HClO_4$ buffer.

As used herein, the BGE comprises an analyte. In an embodiment, the BGE comprises a biological sample as is appropriate for POC assay. In an embodiment, the BGE comprises blood, blood plasma, saliva, urine, sweat, tears, or any other such biofluid or any combination thereof.

In another embodiment, the BGE comprises lake water, fresh water, salt water, wastewater, soil solutions, and the like. The device of the present invention can enrich charged chemical species from any electrolyte solution. For example, the device of the present invention can be used to separate waste from spent hemodialysis fluid, or to extract a compound like a polyaromatic hydrocarbon from water when an ionic surfactant is added to create micelles that bind the hydrocarbon conferring it with charge. Application of the present invention include, and are not limited to, water purification, separation of microplastics, pregnancy test, separation of biological cells, as well as the applications otherwise described within this disclosure.

In some embodiments, the ionically conductive solution has a conductivity from about 1 mS/m (milli-Siemens per meter, wherein a Siemen is the inverse of an Ohms) to about 2 S/m, including every value in between. In an embodiment, a less conductive BGE is selected to avoid rapid hydrogen gas formation, and resulting hydrogen bubbles which limit throughput of the device and methods described herein.

Optical and Non-Optical Detection

As described herein, it is an objective of the disclosure to provide a POC microfluidic device and method of using it that employs electrokinetic focusing of charged analytes driven by a flow-through 3D electrode, or 3D permselective structure, to achieve stable, high-throughput focusing of an analyte coupled to in situ, optical and non-optical (i.e. electrical) sensing.

In an aspect, detection and quantification of the targeted charged species is through optical means. In an aspect, measurements are obtained using a fluorescence microscope and intensities quantified by comparison of IDZ and/or enrichment factor to a subtracted background. As used herein, enrichment factor is the increase in the concentration of the focused species and in an aspect is calculated by comparing the intensity of the brightest region of the enriched area to the initial intensity. In an aspect, enrichment factor is calculated by comparing the intensity of the brightest region of fluorescence in the enriched area to the initial fluorescence intensity. In an embodiment, the binding of a colorimetric indicator aids optical detection. In another embodiment, the binding of a fluorescence marker or dye aids optical detection. In an aspect, optical detection and quantification is through a colorimetric indicator, wherein detection and quantification are visual, for example by the naked eye or a microscope or a camera or a spectrometer or the like. In another aspect detection and quantification is through infrared absorption spectroscopy, ultraviolet absorption spectroscopy, radiometric imaging, Raman spectroscopy, and the like, or combinations thereof. In another aspect, optical detection is aided by separation of a fluorophore and a quencher, or cleavage of a fluorescent substrate by an enzymatic tag. In an embodiment, the device and methods herein employ single or multiple different color fluorophores.

Exemplary methods for optical detection are disclosed in the following articles and are herein incorporated by reference in their entirety: Wang, Y. C.; Han, J. Pre-Binding Dynamic Range and Sensitivity Enhancement for Immuno-Sensors Using Nanofluidic Preconcentrator *Lab Chip* 2008; Cheow et al., Increasing the Sensitivity of Enzyme-Linked Immunosorbent Assay Using Multiplexed Electrokinetic Concentrator, *Anal. Chem.* 2010, 82 (8), 3383-3388; Deng et al. A Novel Thermal Bubble Valve Integrated Nanofluidic Preconcentrator for Highly Sensitive Biomarker Detection,

*ACS Sens.* 2018 3 (7), 1409-1415; and Ko et al., Massively Parallel Concentration Device for Multiplexed Immunoassays, *Lab Chip* 2011, 7.

In an aspect, non-optical sensing is obtained through a change in measured impedance. In an embodiment, impedance is measured using an AC frequency sweep and a Nyquist plot or a Bode plot and the like. In an embodiment, change in impedance is detected by a detectable shift in current-voltage curves ("CVC"). Resistance dictated by ion transport to the electrode or by charge transfer reactions can be observed in the CVC. At low voltages, current increases linearly with the applied potential bias showing ohmic behavior. A further increase in applied voltage leads to ion depletion at the cathodic microband, and the current reaches a limiting value that is reflected by a sharp decrease in the slope of the CVC. Here, increasing voltage leads to growth of the resistive IDZ, preventing further gains in current. At high voltages, rapid vortex flow is initiated within the IDZ leading to a sudden increase in the slope of the CVC, called the overlimiting regime. An exemplary CVC curve, with each zone, is depicted in FIG. 3. In an embodiment, electrical sensing of the enriched analyte is detected through a shift in the CVC observed in which the resistance measured in the over limiting regime is lower than in the absence of enrichment. In an embodiment, the resistance measured is 3-fold lower as indicated by a 3-fold steeper slope of CVC. In another embodiment, change in impedance is detected by a shift in absolute current at a given voltage. In an embodiment, electrical sensing of the enriched analyte is detected through a shift in the CVC observed in the ohmic region. In another embodiment, change in impedance is detected through electrochemical impedance spectroscopy carried out at a voltage within the overlimiting regime.

Based on significant changes in the electronic properties following capture of a charged analyte on the surface of the microbeads in the secondary bead bed, a simple electronic readout can be the platform for detection of analytes at POC. In an embodiment, the analyte is a nucleic acid.

Exemplary methods for non-optical detection are disclosed in the following articles and are herein incorporated by reference in their entirety: Huh et al., Surface Conduction and Electroosmotic Flow Around Charged Dielectric Pillar Arrays in Microchannels, *Lab Chip* 2020, 3; Senapati et al., An Ion-Exchange Nanomembrane Sensor for Detection of Nucleic Acids Using a Surface Charge Inversion Phenomenon, *Biosensors and Bioelectronics* 2014, vol. 60, 92-100; Yin et al., A Non-Optical Multiplexed PCR Diagnostic Platform for Serotype-Specific Detection of Dengue Virus, *Sensors and Actuators* 2020, vol. 310; Slouka et al., Integrated, DC Voltage-Driven Nucleic Acid Diagnostic Platform for Real Sample Analysis: Detection of Oral Cancer, *Talanta* 2015, vol. 145, 35-42; Taller et al., On-Chip Surface Acoustic Wave Lysis and Ion-Exchange Nanomembrane Detection of Exosomal RNA for Pancreatic Cancer Study and Diagnosis, *Lab Chip* 2015, 7; Ramshani et al., Extracellular Vesicle MicroRNA Quantification from Plasma Using an Integrated Microfluidic Device, *Communications Biology* 2019, 189.

Methods of Use

Methods described herein are meant to include any and all aspects and embodiments of the device and invention as described herein. As described herein, an embodiment of a method comprises a BGE solution comprising an analyte which flows into the device through the inlet, through at least one microchannel, and is withdrawn from the outlet. Uniform flow is ensured by any known method. In an embodiment uniform pressure driven flow is ensured by a pump at the inlet to infuse into the device and another pump at the outlet to withdraw the solution from the device. In an embodiment, the BGE solution is infused into the inlet by a syringe and similarly withdrawn from the outlet using a syringe. In an embodiment the flow rate of the BGE through a microchannel is from about 0 mL min$^{-1}$ to about 1 mL min$^{-1}$ and any value in between. In an embodiment, a potential is applied to the inlet and outlet electrodes and the 3D electrode and conductive bead bed. As described above, IDZ formation is driven by charge transfer reactions (fICP) at the surface of the 3D electrode within the microchannel. The 3D electrode efficiently focuses charged species by distributing the IDZ across the cross section of the microchannel.

In an aspect the present invention provides a method for using out-of-plane fICP for high-throughput enrichment, separation, and analysis of an analyte. As used here, the analyte is in a BGE solution. In an embodiment, the BGE solution is a biological sample. The method comprises flowing the BGE solution through the device as described herein. The BGE solution is pumped into at least one inlet, through at least one microchannel wherein the microchannel comprises a 3D electrode as described herein and a secondary bead bed as described herein, and is withdrawn from at least one outlet. A voltage is applied to inlet and/or outlet electrodes and/or the 3D electrode. In an embodiment, an IDZ generated via fICP focuses charged particles in the secondary bead bed. In an embodiment, the charged particles of the BGE solution comprise the analyte. In an embodiment, the secondary bead bed stabilizes fluid flow and enhances focusing of the analyte by augmenting the local electric field strength. In a further embodiment, the secondary bead bed comprises a bead-based assay for an analyte. In another embodiment the analyte is a nucleic acid.

In an aspect the present invention provides a method for using out-of-plane ICP for high-throughput enrichment, separation, and analysis of an analyte. In an embodiment, the analyte is in a biological sample. The method comprises flowing the BGE solution through the device as described herein. In an aspect, the BGE solution is pumped into at least an inlet, through at least one microchannel wherein the microchannel comprises an electrode and permselective membrane coated microbeads as described herein and a secondary bead bed as described herein, and is withdrawn from at least an outlet. A voltage is applied to the inlet and/or outlet electrodes and/or the of the 3D permselective structure. In an embodiment, an IDZ generated via ICP focuses charged particles in the secondary bead bed. In an embodiment, the charged particles of the BGE solution comprise the analyte. In a further embodiment, the secondary bead bed comprises a bead-based assay for the analyte. In an embodiment, the analyte is a nucleic acid.

In an aspect the present invention provides a method of low voltage, POC applications of use. In an embodiment, detection of an analyte is by optical means and/or by non-optical means or a combination thereof. In an aspect, location of the analyte is focused within the secondary bead bed. In an aspect, the present invention provides a method for detecting biomolecules and/or nucleic acids.

In an aspect, the method further comprises detection and quantification of the targeted charged species by optical and/or non-optical means as described herein.

Figure 27:
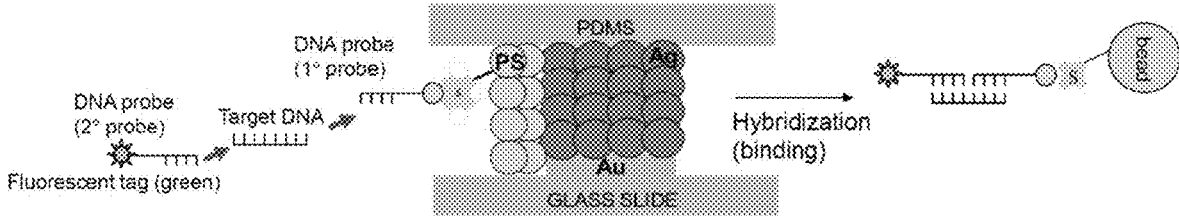
FIG. 27 is an illustration depicting bioconjugated beads in the secondary bead bed bound to a biotin linked to a DNA probe. This probe ("1°") hybridizes to target DNA which in turn hybridizes to a fluorescently-tagged probe ("2°").

In an embodiment, illustrated in FIG. 27, polystyrene ("PS") beads in the secondary bead bed are coated with streptavidin protein ("s") which binds to biotin linked to a DNA probe. This probe ("1°") hybridizes to target DNA which in turn hybridizes to a fluorescently-tagged probe ("2°"). When the device as described here operates, the DNA accumulates within the PS secondary bead bed because it is focused by the electric field. The fluorescently-tagged analyte can then be optically assessed. Further, the analyte may be quantified by electrical means. Electrical detection does not require a fluorescently-tagged probe. The current disclosure is meant to incorporate commercially available bioconjugated and/or probe modified microbeads for likewise in situ quantification of enriched nucleic acids based on either fluorescence or electrical detection.

Figure 26:
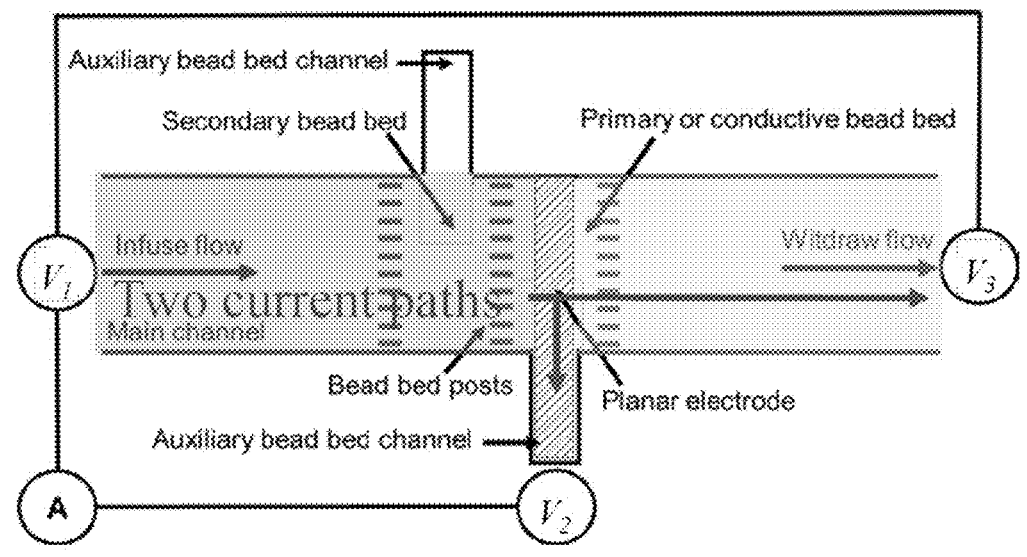
FIG. 26 shows a schematic representation of an embodiment of the device design, near the center of a channel. V is voltage, and A represents an ammeter.

In an aspect, certain voltage patterns may yield more rapid and greater enrichment. In an aspect, the voltage applied to the inlet and outlet electrodes are equal and anywhere from about 1 V to about 250 V, with the electrode and primary bead bed grounded. In another aspect, the electrode at the outlet is set a 0 V with the electrode at the inlet anywhere from about 250 mV to about 250 V. In this embodiment, the applied voltage to the 3D electrode is a sufficient fraction of the inlet electrode voltage to divert current in excess of that required for IDZ formation to the outlet. This fraction will vary depending upon the placement of the 3D electrode or 3D permselective structure within the channel, the conductivity of the BGE both upstream and downstream of the bead bed as downstream the BGE is partly desalted, the activity of the electrode and microbead material for water reduction in the case of fICP, and the conductivity of a permselective coating for counter-ions in the case of ICP. For example, if gas bubbles form at the 3D electrode due to faradaic production of $H_2$ gas or due to joule heating, the voltage bias between the 3D electrode and the outlet can be increased to divert a greater fraction of the current to the outlet to spare the 3D electrode from bubble formation This pattern is illustrated in FIG. 26 for a 1 cm long microchannel with a centrally located 3D electrode and 20 mM Tris.HClO$_4$ buffer. In this aspect, patterns such as V1:V2:V3 of 18:4:0, 20:5:0, 30:10:0, 40:15:0, and similar are employed. This type of voltage pattern may increase the field strength in the inlet segment, which comprises the secondary bead bed, as highlighted by the green area in FIG. 26, and redirect some of the resulting current to the outlet segment as highlighted in yellow in the figure and electrode to avoid excessive current at the planar electrode. Excess current is to be avoided as it may cause electrode damage, heating, and bubble formation. In embodiments wherein the 3D electrode is located nearer the outlet, the patterns have lower voltages on the 3D electrode, such as 18:1:0. In embodiments wherein the conductivity of the BGE is higher, such as blood plasma, the patterns have higher voltages on the 3D electrode, such as 18:11:0. In embodiments wherein the secondary bead bed is longer or filled with smaller beads, then its resistance would require a larger voltage bias between the inlet and 3D electrode, such as 18:1:0. In embodiments wherein the channel is doubled in length, but all else remains the same, the voltage patterns are modified similarly, for example from 18:4:0 to 36:8:0. In an aspect, the voltage is selected such that the 3D electrode is anodic. In an embodiment, the voltage pattern is 0:10:0. In another embodiment the voltage pattern is 0:14:18.

The current disclosure has demonstrated that the structure of the microbeads in the bead bed of the 3D electrode distributes the electric field gradient used for enrichment across the entire channel cross section, thereby facilitating scale-up of channel dimensions without a loss in retention of charged particles or chemical species. The current disclosure further demonstrates that the geometry of the incorporated bead beds (both in the 3D electrode or permselective structure and in the secondary bead bed) mitigate fluid instability that leads to unwanted mixing, as evidenced by smaller vortices with smaller radius of curvature in the IDZ boundary. In some embodiments, the method has a throughput of from about 0.001 mL/h to about 60 mL/h. Furthermore, the current disclosure demonstrates that the device and methods disclosed herein can enrich about 300-fold over 60 minutes, and in some embodiments the enrichment factor is much higher.

The current disclosure has demonstrated that this method offers POC "plug-and-play" enrichment and detection of unlabeled biomolecules because it is compatible with commercially available bioconjugated beads. Incorporation of a secondary bead bed, upstream of the 3D electrode or 3D permselective structure, comprised of probe-modified microbeads facilitates in situ quantification of enriched nucleic acids based on either fluorescence or electrical detection.

All publications, patent applications, issued patents, and other documents referred to in this specification are indicative of the level of ordinary skill in the art to which this invention pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present invention is further illustrated by the following examples, which should not be considered as limiting in any way.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Chemicals, Device Fabrication, and Imaging

Chemicals

The charged fluorophore, BODIPY$^{2-}$ (4,4-fluoro-1,3,5,7, 8-pentamethyl-4-bora-3a,4a-diaza-S-indacene-2,6-disulfonic acid, disodium salt) and Texas Red dye-linked bovine serum albumin ("Texas Red BSA") were obtained from Invitrogen (Carlsbad, Calif.). All other solutions were prepared using reagent grade chemicals (Fisher Scientific, Waltham, Mass.) and diluted with double deionized water ("DDI") (18.2 MΩ·cm, Sartorius Arium Pro, Göttingen, Germany) to desired concentration. SU-8 2050 negative photoresist (Microchem Corp., Westborough, Md.), silicon ("Si") substrate, and polydimethylsiloxane ("PDMS") (Sylgard 184 elastomer kit, Dow Corning Corp., Midland, Mich.) were used for device fabrication. Polystyrene carboxylate ("PSC") beads (diameter, d=20 μm) were purchased from Polysciences Inc. (Warrington, Pa.). Conductive silver-coated hollow glass microbeads (d=10-20 μm, 0.67 g/cc) were purchased from Cospheric (Santa Barbara, Calif.). Gold-coated glass slides with a Cr adhesion layer (1"×3"×0.40"; 50 Å Cr, 1,000 Å Au) were purchased from Evaporated Metal Films (Ithaca, N.Y.) and were used for fabrication of patterned thin film electrodes. Cation selective polymer Nafion™ was purchased from The Chemours Company.

Oligonucleotides used in Example 5 are as follows: Biotin-ATATAAAGAAGTACT TCTGGAGTG (SEQ ID NO: 1) ("1° probe"), AGATCGATGTCTCTTTAGAGC-TAC-FL (SEQ ID NO: 2) ("2° probe"), and BRAF mutant 5'-TATATTTCTTCATGAAGACCT-CACAGTAAAAATAGGTGATTTTGG TCTAGCTA-CAGAGAAATCTCGATGGAGTGGGTCCCATCAGTTT-GAACAGTTGT CTGGATCCATTTTGTGGATGGTAAGAATTGAGGCT-ATTTTTCCACTGATTAAAT TTTTGGCCCT-GAGATGCTGCTGAGTTACTAGAAAGTCATT-GAAGGTCTCAACTATAGT-3' (SEQ ID NO: 4) ("BRAF-Mut"). All oligonucleotide sequences were purchased from Integrated DNA Technologies (Coralville, Iowa). FIG. 23 illustrates the configuration and the oligonucleotide hybridization scheme utilized in the sandwich assay.

Oligonucleotides used in Examples 6 and 7 are as follows: 5'-GTG AGG TCT TCA TGA AGA AAT ATA-3'-Biotin (SEQ ID NO: 5) ("1° probe"), ssDNA 200 base fragment 5'-TAT ATT TCT TCA TGA AGA CCT CAC AGT AAA AAT AGG TGA TTT TGG TCT AGC TAC AGA GAA ATC TCG ATG GAG TGG GTC CCA TCA GTT TGA ACA GTT GTC TGG ATC CAT TTT GTG GAT GGT AAG AAT TGA GGC TAT TTT TCC ACT GAT TAA ATT TTT GGC CCT GAG ATG CTG CTG AGT TAC TAG AAA GTC ATT GAA GGT CT-3' (SEQ ID NO: 6), and 5'-CAT CGA GAT TTC TCT GTA GCT AGA-3'-FAM (SEQ ID NO: 7) ("2° probe").

Device Design, Fabrication, and Operation

Microfluidic devices according to the invention were used in the examples.

The microfluidic devices were fabricated using standard photolithographic processes. Channel molds were patterned using negative photoresist coated on a Si substrate followed by casting with PDMS. The main channel was 19.5 µm tall, 11.0 mm long, and 1.48 mm wide. The width of the bead bed was 0.30 mm, and there were 10.0 µm gaps between the posts used to retain the bead bed. Auxiliary channels used for packing the bead beds were 0.20 mm wide and 2.5 mm long. A 1.0 mm diameter biopsy punch was used to create the inlet and outlet reservoirs of the main channel, and the inlet of the auxiliary channels for bead packing.

Au electrodes were microfabricated on glass slides using standard procedures. The patterned Au electrode width was 0.2 mm and it was centered at the midpoint of the main channel, underneath the primary or conductive bead bed. This electrode was sufficiently long to extend out from under the PDMS monolith to make contact to a wire lead. The PDMS layer and glass slide with patterned Au film were treated in an air plasma (PDC-001, Harrick Plasma, Ithaca, N.Y.) for 60 seconds and then placed in contact to bond. To enhance the bond strength, the device was incubated at 65° C. for at least 18 hours.

If employed, a suspension of the conductive Ag-coated beads in DDI (5.0 µL, w/v=22 mg mL$^{-1}$) was packed into the primary bead bed by pipetting them into the inlet and applying pressure. The 300 µm-wide primary bead bed is defined by a row of narrowly spaced posts with 10.0 µm gaps. When a secondary bead bed was used, a suspension of PSC beads (10 µL, 10 v/v % in DDI) was packed into the inlet of the auxiliary channel of the secondary bead bed using the same method. The 500 µm-wide secondary bead bed is defined by a row of narrowly spaced posts with 10.0 µm gaps. The inlets of these auxiliary channels were then sealed by adding a drop (approximately 40 µL) of PDMS. In the case that bioconjugated beads were utilized in the secondary bead bed, the PDMS in these inlets was cured at room temperature for at least 18 h. Otherwise, the PDMS was cured by incubating the device at 65° C. for 3 hours. Devices were filled with 40.0 mM Tris.HClO$_4$ buffer prior to use. The electrodes at the inlet and outlet were comprised of 1 mm O.D. stainless steel tubing that connected the inlet and outlet of each device to PTFE tubing. A second exemplary device design with increased width of the main channel (3.0 mm), was used to demonstrate scalability of out-of-plane fICP devices. The dimensions for both devices are summarized in Table 1.

Flow through exemplary devices was established using two syringe pumps (Pico Pump Elite, Harvard apparatus, Holliston, Mass.), each of which were equipped with a glass syringe (500 µL) connected to the device with 1.0 mm internal diameter PTFE tubing. Uniform pressure driven flow was ensured by setting one pump to infuse into the inlet and the other pump to withdraw from the outlet reservoir.

Voltage was applied, and current measured, by a 6487 Picoammeter/Voltage source (Keithley, Cleveland, Ohio) and current was recorded using ExceLINX (Keithley, Cleveland, Ohio)

TABLE 1

Exemplary device dimensions.

| Exemplary Device Design | Channel Width, mm | Channel Length, mm | Channel Height, µm | Primary or Conductive Bead Bed Width, µm | Secondary Bead Bed Width, µm | Gap Between Bead Bed Posts, µm |
|---|---|---|---|---|---|---|
| 1 | 1.48 | 11.0 | 40 ± 0.5 | 300 | 500 | 10 |
| 2 | 3.00 | 11.0 | 40 ± 0.5 | 300 | 500 | 10 |

Fluorescence Imaging and Data Processing

All fluorescence measurements were obtained using an Eclipse Ti-S inverted fluorescence microscope (Nikon Industries, New York, N.Y.) equipped with a digital camera (Orca Flash 4.0, Hamamatsu Corp., Bridgewater, N.J.). All images were processed using NIS-Elements 4.6 software (Nikon) and ImageJ (NIH). Fluorescence intensities used for quantitative comparison of IDZ growth and for calculation of EF were background subtracted and processed using MatLab (The MathWorks Inc. Natick, Mass.) and NIS-Elements 4.6 software.

Example 1

Confirmation of Ion Depletion Zone by the fICP Mechanism

In this Example, the presence or absence of an IDZ was determined for three distinct background electrolyte ("BGE") solutions.

Exemplary devices were fabricated using the processes as outlined above, and according to FIG. 1, using the dimensions of Exemplary Device Design 1 in Table 1, and a planar Au microband electrode with no beads. In this Example, the main channel was rinsed for 20 minutes with 40.0 mM Tris.HClO$_4$ buffer solution before filling the inlet reservoir with 10.0 µL of a BGE solution spiked with 0.3 µM Texas Red BSA and 10 µM BODIPY$^{2-}$. The BGE solutions tested include KNO$_3$ (10.0 mM, 1588 µS cm$^{-1}$), phosphate buffer (10.0 mM, pH 7.4, 2642 µS cm$^{-1}$), and Tris.HClO$_4$ buffer (40.0 mM, pH 8.3, 878 µS cm$^{-1}$). Prior to use, devices were conditioned at 3.0 V for 5 minutes, at 200 nL min$^{-1}$. For ion depletion zone ("IDZ") growth measurements, the flow rate was decreased to 10 nL min$^{-1}$ allowing the flow to equilibrate for 10 minutes. Then, a potential between 0 V and 15.0 V was applied and the current measured between the inlet and outlet electrodes and Au microband. After each trial, the device was rinsed thoroughly with DDI, followed by BGE solution.

Figure 5:
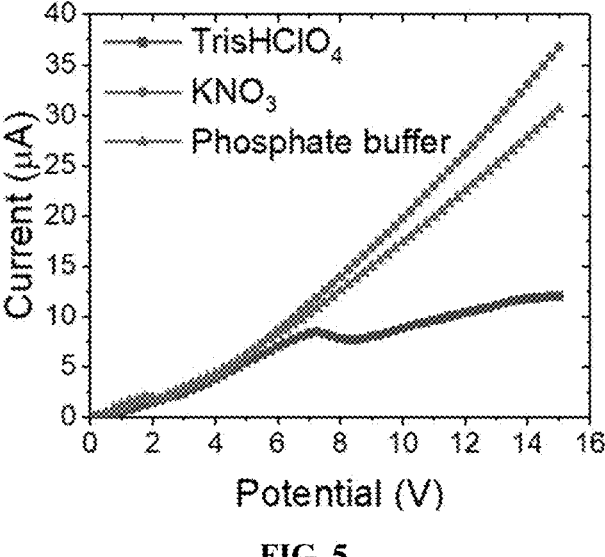
FIG. 5 depicts current-voltage curves for three different background electrolyte solutions: 40.0 mM Tris.HClO$_4$ buffer, 10.0 mM KNO$_3$, and 10.0 mM phosphate buffer using the planar Au device with no beads.

FIG. 5. depicts current-voltage curves ("CVC") obtained for the three different solutions—Tris.HClO$_4$ buffer (40.0 mM), KNO$_3$ (10.0 mM) and phosphate buffer (10.0 mM) using the planar Au device with no beads. Ohmic, limiting, and overlimiting regions, corresponding to three distinct slopes were observed only in the Tris.HClO$_4$ buffer solution. The anion of the Tris buffer, Trial$^+$, reacts with OH$^-$ to form an uncharged species, thus neutralizing the buffer ions comprising the BGE. This removal of ions of the BGE results in a local decrease in ionic strength and creation of an IDZ. The anions of the other two BGE solutions, NO3$^-$ and HPO4$^{2-}$/H$_2$PO$_4^-$, do not react with OH$^-$ to form an uncharged product and thus do not form an IDZ.

Figure 6A:
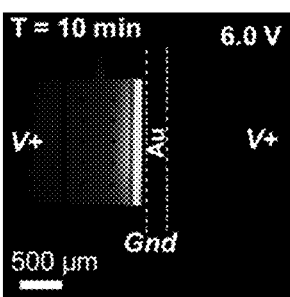
FIG. 6A shows a fluorescence micrograph of a background electrolyte spiked with 10 μM BODIPY$^{2-}$ after 10 minutes following the application of V+=6.0 V.
Figure 6B:
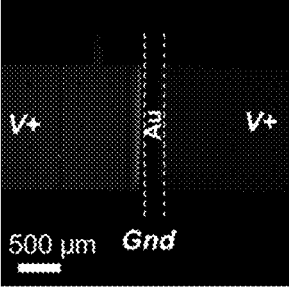
FIG. 6B shows a fluorescence micrograph of a background electrolyte spiked with 0.3 μM Texas Red Bovine Serum Albumin after 10 minutes following the application of V+=6.0 V.
Figure 6C:
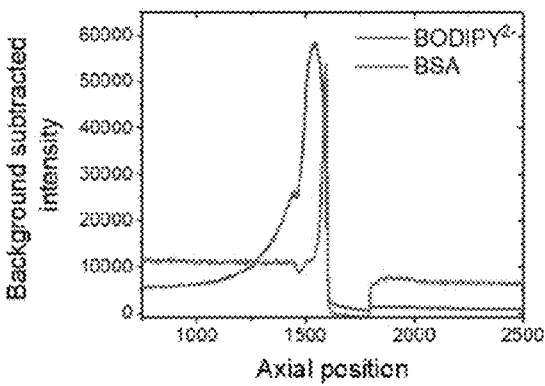
FIG. 6C depicts background subtracted fluorescence intensities measured along cut lines located across the ion depletion zone boundary in the images shown in FIG. 6A and FIG. 6B.
Figure 7:
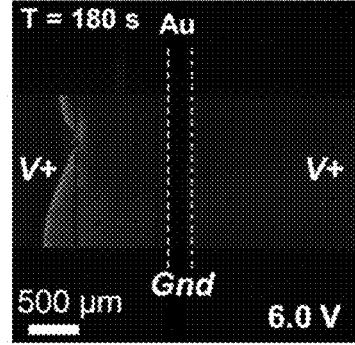
FIG. 7 shows a fluorescence micrograph demonstrating stacking of dye-linked albumin in KNO$_3$ solution (10.0 mM) under applied potential of 6.0 V.

Additionally, the distribution of the two anionic dyes in these solutions under conditions appropriate for electrokinetic enrichment was evaluated. First, the channel was filled with the BGE, 40.0 mM Tris.HClO$_4$ buffer, and then a constant flow rate of 100 nL min$^{-1}$ was established by a syringe pump connected to the inlet reservoir. Next, a voltage bias of V+=6.0 V was applied between an electrode in the microchannel inlet and a wire lead connected to the Au microband. Finally, a series of fluorescence micrographs was obtained to monitor the distribution of the dyes. FIG. 6A and FIG. 6B are fluorescence micrographs obtained following 10 minutes of enrichment for BODIPY$^{2-}$ and Texas Red bovine serum albumin (BSA), respectively. The anionic dyes accumulated upstream of the microband, indicating that an IDZ and electric field gradient have formed. Since each dye is focused at an axial location at which its electrophoretic and convective velocities are equal, but opposite, BODIPY$^{2-}$, which has a higher electrophoretic mobility, forms an enriched plug further upstream than does the dye-linked albumin as shown in FIG. 6C. Focusing of these dyes by fICP was not observed in KNO$_3$ or phosphate buffer solutions. However, the dye-linked albumin accumulated upstream of the Au microband cathode in KNO$_3$ solution, a result attributed to isoelectric focusing of the protein following the formation of a pH gradient. It is thought that the pH gradient was generated by water electrolysis at the inlet and outlet electrodes and planar Au electrode. This accumulation of dye-linked albumin is depicted in FIG. 7.

Figure 8:
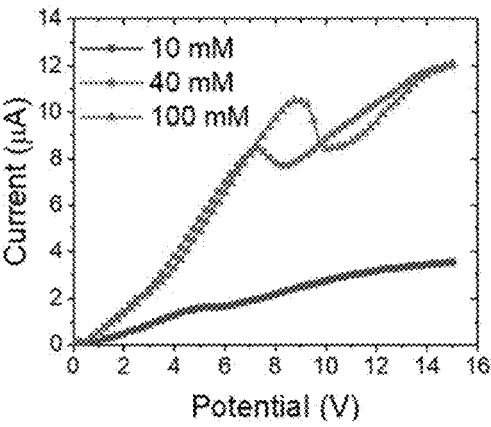
FIG. 8 is a current-voltage curve for differing concentrations of Tris.HClO$_4$ buffer background electrolyte solution.

CVC characteristics obtained at a planar Au electrode as a function of the concentration of Tris.HClO$_4$ buffer were next investigated. FIG. 8 shows CVCs obtained in 10.0 mM, 40.0 mM, and 100.0 mM Tris.HClO$_4$ buffer solutions under low flow conditions (10 µL min$^{-1}$) with the voltage stepped in 0.25 V increments every 0.33 second. Each curve exhibits clear variations in the slope that delineate the three characteristic regimes as illustrated in FIG. 3. A shift in the onset of limiting and overlimiting behavior to higher voltages is observed with increasing Tris.HClO$_4$ buffer concentration. Further confirming the presence of an IDZ by the fICP mechanism.

Example 2

IDZ Formation with 3D Electrode Structures for fICP with and without a Secondary Upstream Bead Bed In this Example, IDZ formation at the planar Au microband electrode is compared with devices having a three-dimensional electrode in the absence ("Ag/Au") and presence ("PSC/Ag/Au") of a secondary, upstream PSC bead bed.

Exemplary devices were fabricated using the processes as outlined above, according to FIG. 1, and using the dimensions of Exemplary Device Design 1 in Table 1. Three exemplary device structures were examined: a device with a planar Au microband electrode and no beads, a device with a 3D electrode comprised of a planar Au microband and Ag beads, and a device with the 3D electrode and an upstream secondary bead bed of PSC beads. These device structures are illustrated in FIG. 4A, FIG. 4B, and FIG. 4C.

Figure 9A:
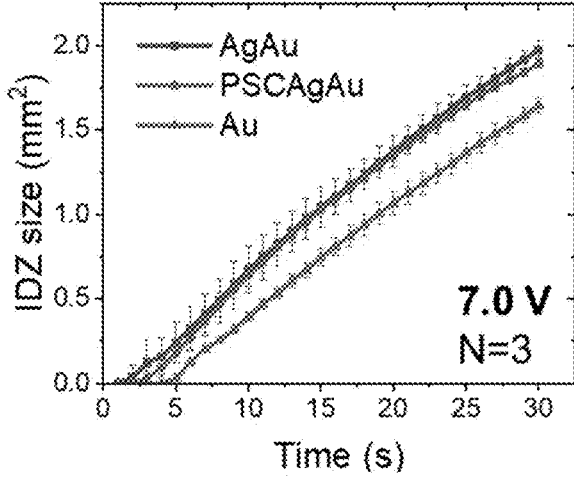
FIG. 9A depicts a plot of the projected area of the ion depletion zone as a function of time for a planar Au microband electrode ("Au"), a 3D electrode (planar Au microband electrode with Ag microbeads) ("AgAu"), and a 3D electrode with a secondary upstream bead bed ("PSCAgAu"). A voltage bias of 7.0 V was applied.
Figure 9B:
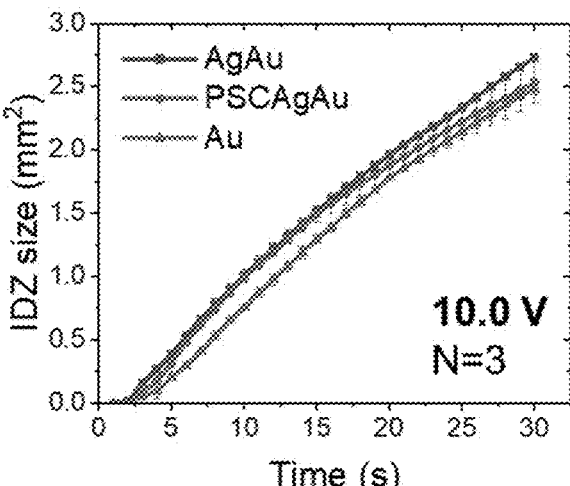
FIG. 9B depicts a plot of the area of the ion depletion zone as a function of time for a planar Au microband electrode ("Au"), a 3D electrode (planar Au microband electrode with Ag microbeads) ("AgAu"), and a 3D electrode with a secondary upstream bead bed ("PSCAgAu"). A voltage bias of 10.0 V was applied.

In this Example, the main microchannel was rinsed for 20 minutes with Tris.HClO$_4$ buffer (40.0 mM, pH 8.3). The reservoirs were then filled with 40.0 mM Tris.HClO$_4$ buffer solution with 10.0 µM BODIPY$^{2-}$. Prior to use, devices were conditioned for 5 minutes at 3.0 V under a flow rate of 200 nL min$^{-1}$. As described above, uniform pressure driven flow was ensured using infusion and withdrawal from the inlet and outlet reservoirs, respectively. Prior to IDZ growth measurements, the flow rate was decreased to 10 nL min$^{-1}$ and allowed to equilibrate for 10 minutes. To initiate fICP, a voltage bias of 5.0 V was applied and the area of the IDZ was measured as the region over which the fluorescence intensity was ≤0.5-fold the initial fluorescence intensity. These measurements were repeated at a voltage bias of 7.0 and 10.0 V. Between each of these experiments, the device was refreshed by increasing the flow rate to 200 nL min$^{-1}$ for 20 seconds. The flow rate was once again decreased to 10 nL min$^{-1}$ and allowed to equilibrate for 10 minutes. The plots of IDZ size as a function of time at 7.0 V and 10.0 V is shown in FIG. 9A and FIG. 9B and in FIG. 11 at 5.0 V. Fluorescence micrographs showing the distribution of the tracer at 0, 5, 20, and 30 seconds following application of V+=5.0 V are depicted in FIG. 10A, FIG. 10B, and FIG. 10C.

Figure 10A:
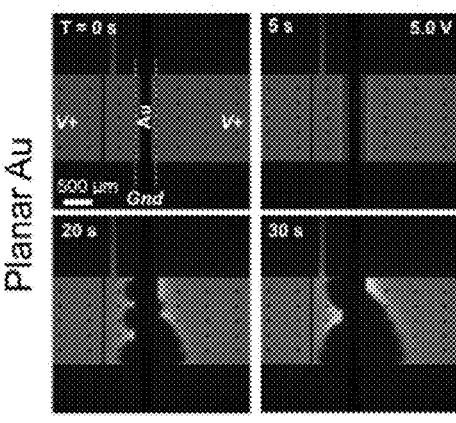
FIG. 10A depicts ion depletion zone growth over time for a planar Au microband electrode under an applied voltage of 5.0 V in a solution of 10 µM BODIPY$^{2-}$ in 40.0 mM Tris.HClO$_4$ buffer background electrolyte solution.
Figure 10B:
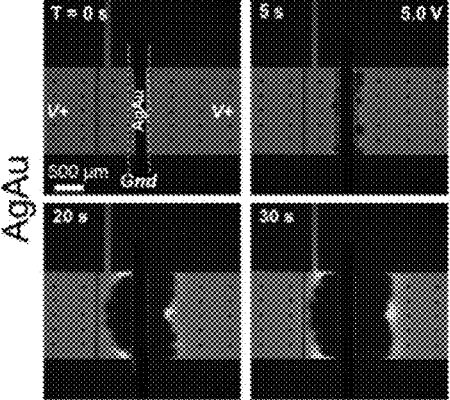
FIG. 10B depicts ion depletion zone growth over time for a 3D electrode (planar Au microband electrode with Ag microbeads) under an applied voltage of 5.0 V in a solution of 10 µM BODIPY$^{2-}$ in 40.0 mM Tris.HClO$_4$ buffer background electrolyte solution.
Figure 10C:
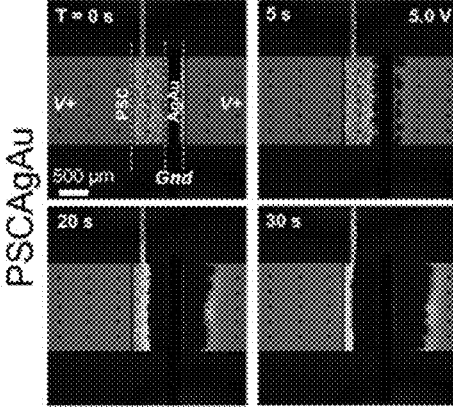
FIG. 10C depicts ion depletion zone growth over time for a 3D electrode (planar Au microband electrode with Ag microbeads) with a secondary upstream PSC bead bed under an applied voltage of 5.0 V in a solution of 10 µM BODIPY$^{2-}$ in 40.0 mM Tris.HClO$_4$ buffer background electrolyte solution.
Figure 11:
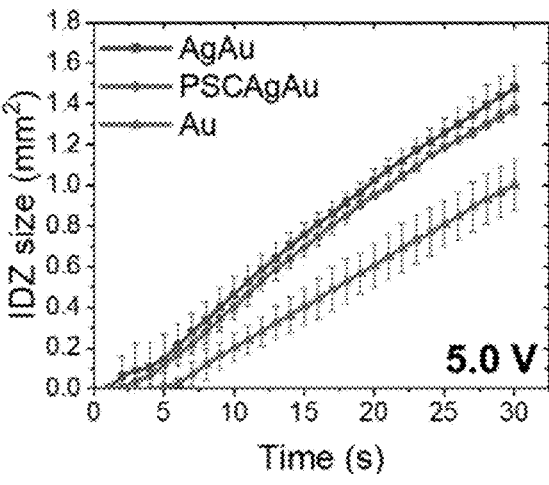
FIG. 11 depicts ion depletion zone growth as a function of time for planar Au microband electrode, a 3D electrode (planar Au microband electrode with Ag microbeads), and a 3D electrode with a secondary upstream bead bed. A voltage bias of 5.0 V was applied.

As shown in FIG. 10A, the planar Au device exhibits larger vortices indicated by larger radius of curvature in the IDZ boundary. In the Ag/Au device, many smaller vortices with smaller radius of curvature are observed as depicted in FIG. 10B. Additionally, based on measurements of the area of the IDZ, FIG. 11, the onset time for stable IDZ growth is earlier for the Ag/Au structure (1 second) versus the planar Au system (5 seconds). This later onset for a planar electrode alone is attributed to the lag time required for the IDZ to extend to the full height of the channel before propagating upstream and downstream from the planar electrode. FIG. 10C depicts the evolution of the IDZ in the presence of a secondary bead bed located upstream of the conductive (Ag) bead bed. The IDZ boundary has a stable, plug-like shape and was maintained within the secondary bead bed and did not propagate further upstream. The IDZ growth over time is comparable to the Ag/Au system as per FIG. 11. The increase in time to the initiation of the IDZ for the PSC/Ag/Au system of about 2 seconds is attributed to an increase in the overall resistance of the device due to the volume occupied by the PSC beads. Faster IDZ growth is observed for all device designs with increased potential as shown in FIG. 9A and FIG. 9B. FIG. 9A and FIG. 9B also indicate that the difference in IDZ growth decreases between device structures as applied potential is increased.

Figure 12A:
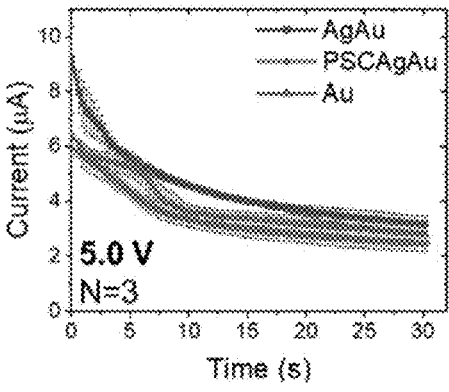
FIG. 12A demonstrates current transients for planar Au microband electrode, a 3D electrode, and a 3D electrode with a secondary upstream bead bed at 5.0 V.
Figure 12B:
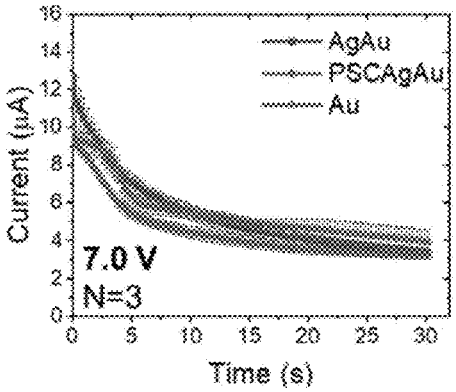
FIG. 12B demonstrates current transients for planar Au microband electrode, a 3D electrode, and a 3D electrode with a secondary upstream bead bed at 7.0 V.
Figure 12C:
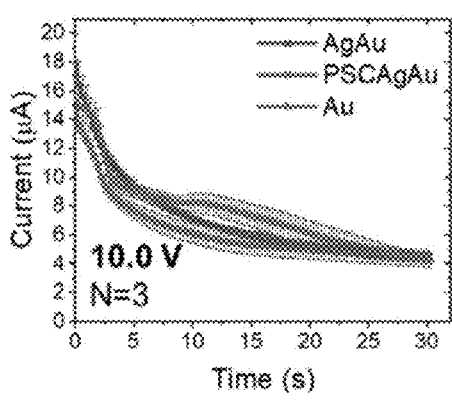
FIG. 12C demonstrates current transients for planar Au microband electrode, a 3D electrode, and a 3D electrode with a secondary upstream bead bed at 10.0 V.

Current transients and CVCs were compared for the three device structures with the microchannel filled with 40.0 mM Tris.HClO$_4$ buffer solution. First, the electrodes at the inlet and outlet and Au planar microband were connected by power supply in series with a picoammeter. Then, 5.0 V was applied. The resulting current at the electrode was measured for 30 seconds using ExceLINX software. Further, the device was rinsed according to the procedure described above before repeating at 7.0 and 10.0 V. FIG. 12A, FIG. 12B, and FIG. 12C show these current transients for each architecture. The current transient obtained for the planar Au electrode shows a stepwise decay, while both 3D structured electrodes exhibit gradual decay. This stepwise decay is attributed to initial growth of the IDZ in the z-direction from the planar electrode until it makes contact with the channel 'ceiling' which then leads to a sudden increase in resistance, indicated by a drop in the current, followed by outward propagation.

Figure 13:
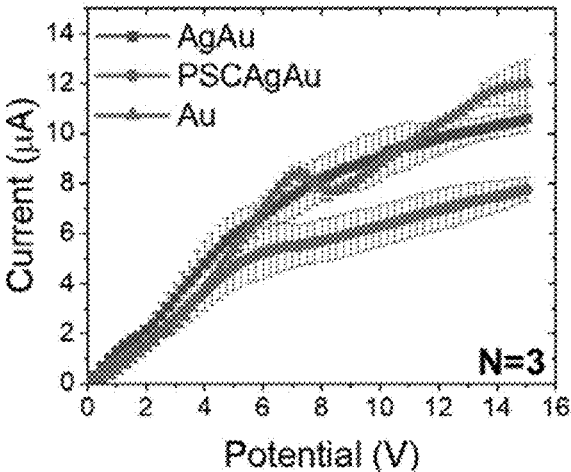
FIG. 13 depicts current-voltage curves for planar Au microband electrode, a 3D electrode, and a 3D electrode with a secondary upstream bead bed.

To evaluate the current-voltage relationship of each structure, the electrodes at the inlet and outlet and planar Au microband were connected by a power supply in series with a picoammeter. Then, a series of voltage steps from 0 V to 20.0 V were applied in 0.25 increments at a rate of 0.33 second per step. The resulting current at the electrode was measured for 26 seconds using ExceLINX software. Between each CVC, the device was rinsed according to the procedure described above. FIG. 13 depicts the CVCs obtained for the three structures. In the planar Au device, three distinct regions are observed in the CVC. In the Ag/Au device, there is a direct transition from the ohmic to the overlimiting regime. The PSC/Ag/Au device yields a comparable CVC to the Ag/Au device, but the currents are shifted lower due to increased overall resistance.

Figure 14A:
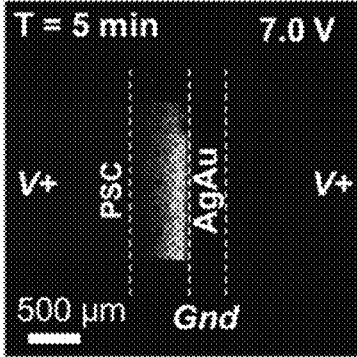
FIG. 14A shows a fluorescence micrograph obtained after 5 minutes of enrichment of BODIPY$^{2-}$ in the device with a 3D electrode ("AgAu") and a secondary upstream bead bed ("PSC").
Figure 14B:
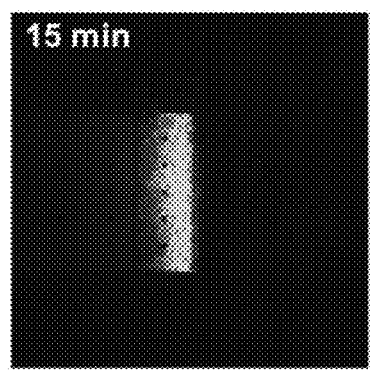
FIG. 14B shows a fluorescence micrograph obtained after 15 minutes of enrichment of BODIPY$^{2-}$ in the device with a 3D electrode ("AgAu") and a secondary upstream bead bed ("PSC").
Figure 15:
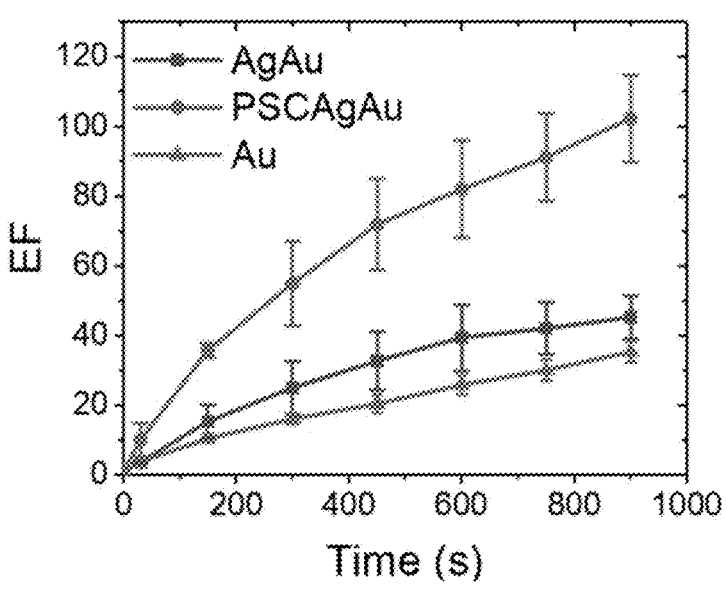
FIG. 15 is a plot of enrichment factor as a function of time for planar Au microband electrode, a 3D electrode, and a 3D electrode with a secondary upstream bead bed.

The ability of each device to focus a charged species was next evaluated. First, the channel was filled with 0.1 μM BODIPY$^{2-}$ in 20.0 mM Tris.HClO$_4$ buffer (pH 8.3), which was kept under constant flow at 100 nL min$^{-1}$. Then, a potential of V+=7.0 V was applied between both inlet and outlet electrodes and the electrode within the microchannel. FIG. 14A and FIG. 14B depict fluorescence micrographs showing the enrichment of BODIPY$^{2-}$ in the PSC/Ag/Au device obtained at 5 minutes and at 15 minutes after applying the voltage. FIG. 15 is a plot of enrichment factor ("EF") as a function of time observed in the three device architectures. EF was calculated by comparing the brightest region of the enriched plug (an average of 10 neighboring pixels) to the initial fluorescence intensity. Fluorescence intensities were background subtracted. The EF of an enriched plug confined to the PSC bead bed was calculated by comparing to the initial intensity measured within the bed. These results indicate that higher EF, up to 115-fold within 15 minutes, can be obtained by employing the PSC/Ag/Au device, in comparison to Au or Ag/Au, for which EFs of 30- and 40-fold were obtained, respectively. The increased enrichment observed with the addition of a Ag bead-bed electrode to the Au microband is attributed to the full height of the electrode and its stabilization of the IDZ. This difference is expected to become more dramatic as the height of the microchannel is increased. The PSC/Ag/Au device yields a greater increase in the rate of enrichment for two reasons. First, the PSC bead bed provides fluidic stabilization within the entire IDZ volume by geometric restriction and surface conduction mechanisms. Second, both the fluid velocity and the electric field are enhanced in the bead-occupied channel segment due to its increased fluidic and electrical resistance. Dispersion is also expected to be mitigated by the beads.

Example 3

Scalability of the Device

In this Example, the impact of device scale on concentration enrichment in the PSC/Ag/Au device is investigated.

Figure 16:
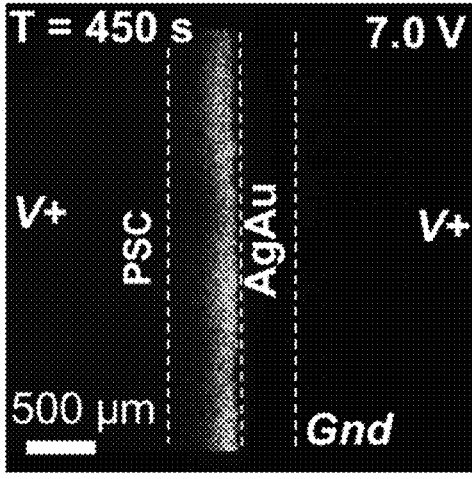
FIG. 16 is a fluorescence micrograph showing an enriched band of BODIPY$^{2-}$ 450 seconds after initiation of an applied voltage of 7.0 V in the PSC/Ag/Au device.
Figure 17:
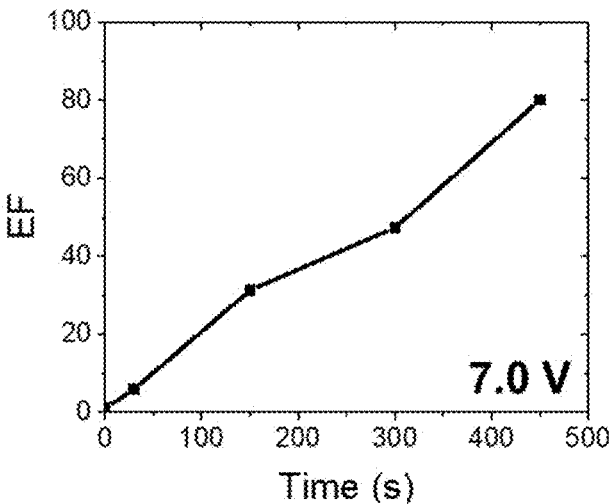
FIG. 17 is a plot of enrichment factor ("EF") as a function of time after initiation of an applied voltage of 7.0 V in the PSC/Ag/Au device.

Exemplary devices were fabricated using the processes as outlined above, according to FIG. 1, using the dimensions of Exemplary Device Design 2 in Table 1. Both the flow rate and channel width were doubled as compared to the Exemplary Device Design 1 in the previous Examples. The channel was filled with 0.1 μM BODIPY$^{2-}$ in 40.0 mM Tris buffer, and constant fluid flow was established. Then, V+=7.0 V was applied. FIG. 16 is a fluorescence micrograph of the resulting enriched band of tracer dye positioned within the PSC bead bed after 450 seconds following initiation of the applied voltage. FIG. 17 shows the evolution of the EF over this time period. The 80-fold enrichment obtained over 450 seconds is a rate of 0.18-fold/s, which is comparable to the rate (0.13-fold/s) observed in the narrower (1.48 mm-wide) device. This result indicates that out-of-plane fICP is scalable. Over longer periods of time, hydrogen gas bubble formation disrupts the IDZ boundary, which leads to a decrease in the enrichment of charged species. To avoid rapid hydrogen gas formation, a less conductive BGE can be employed. Alternatively, the voltage (V+) can be applied to the inlet or outlet alone, and the other left floating, instead of being applied to both, so that the bead bed/microband electrode does not have to support the current from both halves of the device.

Example 4

IDZ Growth in a Device Utilizing More than one Secondary Bead Bed

In this Example, the impact of more than one secondary bead bed on IDZ growth is investigated.

Figure 18:
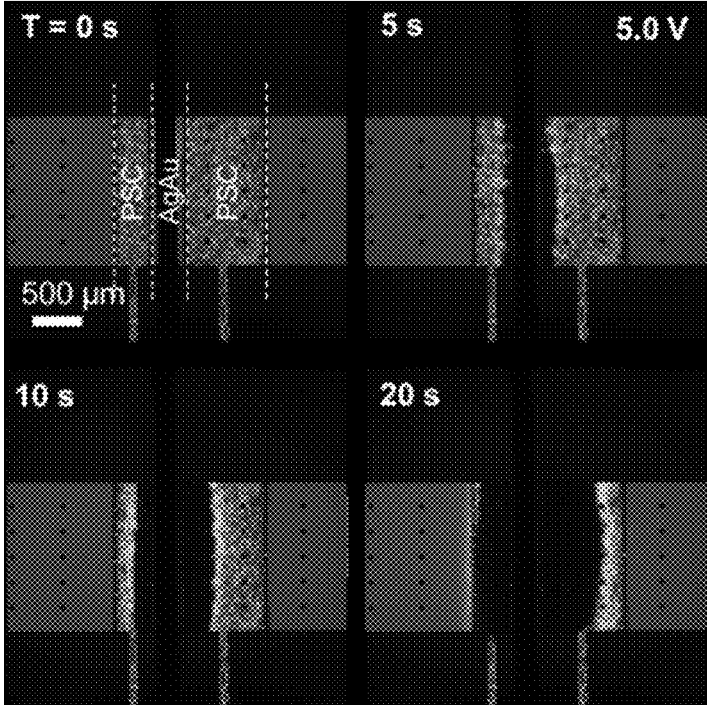
FIG. 18 depicts fluorescence micrographs showing the ion depletion zone at time 0, 5, 10 and 20 seconds in a device with two polystyrene carboxylate bead beds flanking the 3D Ag/Au electrode.

Exemplary devices were fabricated using the processes as outlined above, according to FIG. 1, using the dimensions of Exemplary Device Design 1 in Table 1 with the addition of another secondary bead bed downstream from the electrode. This downstream bead bed was filled with PSC beads according to the above described procedure for filling the upstream secondary bead bed. The microchannel was filled with 0.1 μM BODIPY$^{2-}$ in 40.0 mM Tris.HClO$_4$ buffer, which was kept under constant flow at 10 nL min$^{-1}$. Then, a potential of V+=5.0 V was applied between both inlet and outlet electrodes and the electrode within the microchannel. FIG. 18 shows IDZ growth in a device having two secondary PSC bead beds flanking the 3D Ag/Au electrode. Comparing FIG. 18 to FIGS. 10A, 10B, and 10C indicates that further stabilization of the IDZ boundary can be achieved by flanking the 3D electrode on both sides with secondary structures of bead beds. However, by adding secondary bead beds, overall resistance of the device increases.

Example 5

Enrichment of Nucleic Acids Coupled with a Bead-Based Assay

In this Example, the ability to interface a focused band of analyte within the secondary bead bed with a bead-based assay is examined.

Attachment of the Biotinylated Oligonucleotide to Steptavidin Coated Microbeads.

Biotinylated oligonucleotide (1° probe) was bound to streptavidin-modified beads following a standard procedure. First, 100 μL of the bead suspension (Bangs Laboratories, Fishers, Ind.) was rinsed two times with 100 μL of a wash buffer (20.0 mM Tris.HClO$_4$ buffer, pH 7.5, 1.0 M NaCl, 1.0 mM EDTA, and 0.0005% Triton™ X-100) by centrifuging the beads at 5000 rpm for 3 minutes, and decanting the supernatant. Second, the beads were resuspended into 20 μL of wash buffer and 7.6 μg of 1° probe. The beads were incubated at 800 rpm (ThermoMixer C, Eppendorf, Hauppauge, N.Y.) for 30 min at 20° C. Third, unbound 1° probe was removed by rinsing two times with 100 μL of the wash buffer, centrifuging the beads at 5000 rpm for 3 min, and decanting the supernatant. Lastly, these oligo-bound microbeads were re-suspended in 100 μL of wash buffer and stored at 4° C.

Exemplary devices with a 3D electrode of a planar Au microband and Ag microbeads were fabricated using the processes as outlined above, according to FIG. 1, using the dimensions of Exemplary Device Design 1 in Table 1. The PDMS for this Example was cured at room temperature overnight to prevent degradation of the modified PSC beads. The PSC beads for the secondary bead bed as described above were replaced with streptavidin-coated 15 μm diameter PSC microbeads modified with a biotinylated oligonucleotide probe ("1° probe") as described above. The sequence of this probe was designed to be complementary to the 5' end of the V600E BRAF mutant ("BRAF-Mut") gene, which has a high prevalence in melanoma (about 45% of patients). This is depicted in FIG. 23. A secondary probe ("2° probe"), complementary to the mutant strand and tagged with fluorescein ("FL"), was included to aid in fluorescence-based detection. The targeted gene encodes the BRAF enzyme, which participates in a signaling pathway responsible for cell growth. The V600E mutation leads to increased activity of the BRAF enzyme, and ultimately causes uncontrolled growth and spread of tumor cells. The detection of this mutation in tumor tissue or as circulating tumor DNA ("ctDNA") in blood plasma has diagnostic value and is a pharmacodynamic indicator for treatment with drugs that inhibit BRAF enzyme.

An assay for BRAF-Mut proceeded as follows. First, the channel was filled with 20.0 mM Tris.HClO$_4$ buffer, and a fluorescence image was obtained. Second, the channel was infused with a solution containing 0.4 μM 2° probe and 20 pM BRAF-Mut single-stranded DNA ("ssDNA") in 20.0 mM Tris.HClO$_4$ buffer ("assay solution") at a flow rate of 100 nL min$^{-1}$. This flow rate was maintained for 60 minutes, and then the channel was rinsed with 20.0 mM Tris.HClO$_4$ buffer solution and an additional fluorescence image obtained. Third, the assay solution was introduced into the channel again, and a constant flow rate of 100 nL min$^{-1}$ was established. Then, V+=7.0 V was applied between the inlet and outlet electrodes and the wire lead connected to the 3D Ag/Au electrode, and accumulation of the FL-tagged 2° probe was monitored by fluorescence microscopy. Finally, the applied voltage was released and the device was rinsed with a buffer solution for 10 minutes to remove non-specifically bound nucleic acids before a final fluorescence image was obtained.

Figure 19A:
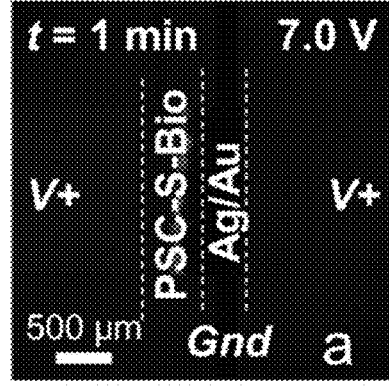
FIG. 19A shows a fluorescence micrograph depicting co-enrichment of the FITC-tagged 2° probe and BRAF-Mut ssDNA at 1 minute following initiation of an applied voltage of V+ to a device with a 3D electrode and a secondary bead bed wherein the PSC beads were modified with the 1° probe.
Figure 19B:
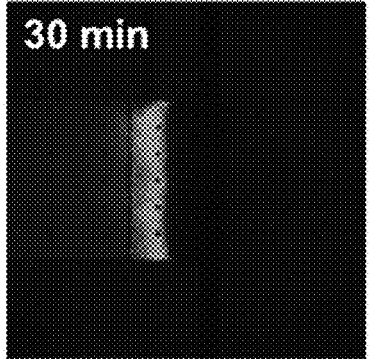
FIG. 19B shows a fluorescence micrograph depicting co-enrichment of the FITC-tagged 2° probe and BRAF-Mut ssDNA at 30 minutes following initiation of an applied voltage of V+ to a device with a 3D electrode and a secondary bead bed wherein the PSC beads were modified with the 1° probe.
Figure 19C:
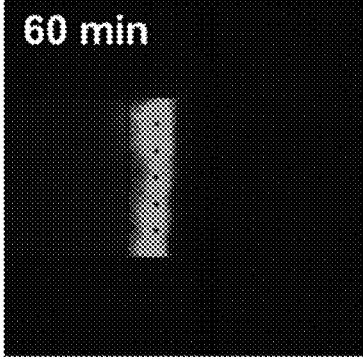
FIG. 19C shows a fluorescence micrograph depicting co-enrichment of the FITC-tagged 2° probe and BRAF-Mut ssDNA at 60 minutes following initiation of an applied voltage of V+ to a device with a 3D electrode and a secondary bead bed wherein the PSC beads were modified with the 1° probe.
Figure 20:
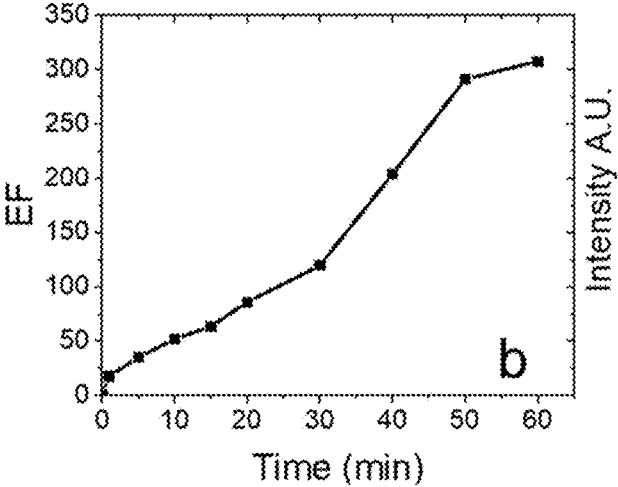
FIG. 20 is a plot of enrichment factor as a function of time observed for the 2° probe.
Figure 21:
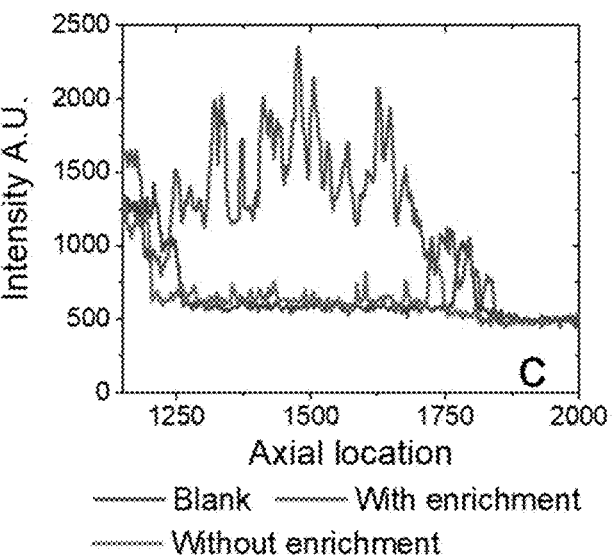
FIG. 21 shows background subtracted intensity profiles taken across the midline of the 1° probe-modified bead bed before ("Blank") and after ("Without enrichment") 60 minutes of exposure to the assay solution and after 60 minutes of fICP-based enrichment of the 2° probe and BRAF-Mut within the bead bed ("With Enrichment").

FIGS. 19A, 19B, and 19C are a time series of fluorescence micrographs demonstrating the formation of an enriched plug of the FL-tagged 2° probe within the 1° probe-modified bead bed at 1, 30, and 60 minutes after application of the voltage bias. FIG. 20 is a plot of the calculated EF as a function of time. 300-fold enrichment of the 2° probe was achieved within 60 minutes. FIG. 21 show fluorescence intensity profile taken across the midline of the bead bed prior to ("blank") and after ("Flow assay") 60 minutes of exposure of the beads to the assay solution in the absence of electrokinetic enrichment. This plot also shows the intensity profile obtained following 60 minutes of fICP-based enrichment of the assay solution ("fICP assay"), followed by rinsing. There was not a significant difference observed between the signals obtained for the blank and 20 pM BRAF-Mut in the absence of enrichment, but this concentration of BRAF-Mut was readily detected following 60 minutes of enrichment by fICP. This demonstrates enhanced sensitivity of a bead-based nucleic acid assay by faradaically-driven electrokinetic enrichment at a 3D flow-through electrode. This finding is significant because the device can be readily prepared from commercially available metallic and bioconjugated beads, making it a plug-and-play platform for sensitive bioassays.

Next, a non-optical approach to sense the analyte following hybridization to the probe-modified beads was investigated. CVCs were evaluated to serve as a non-optical sensing mechanism for hybridization of ssDNA, using the BRAF-Mut as a model system.

Figure 22:
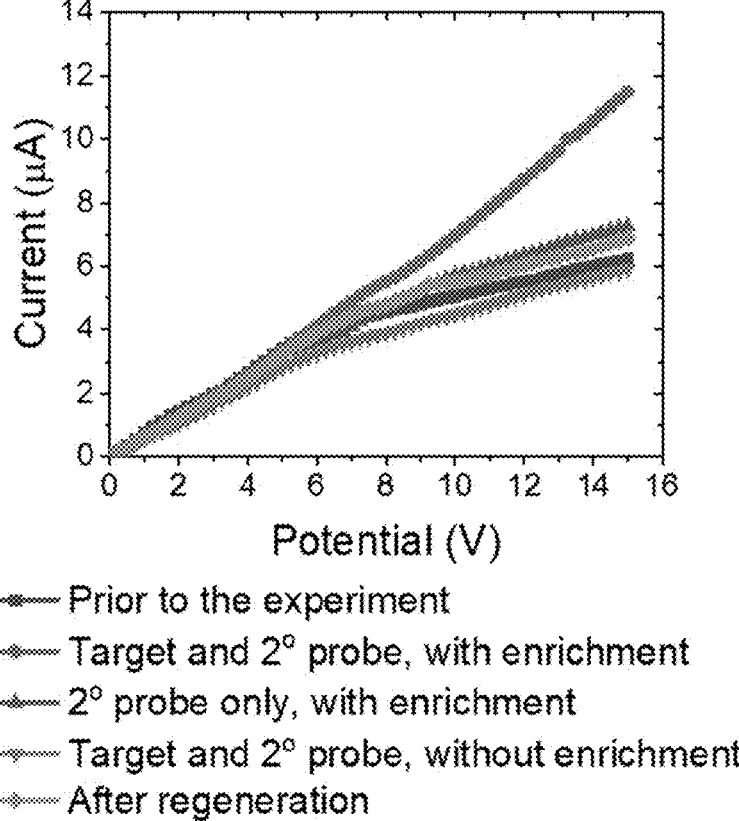
FIG. 22 depicts current-voltage curves for the device filled with a Tris.HClO$_4$ buffer solution ("Prior to the experiment"), after flowing the assay solution for 60 minutes ("Target and 2° probe, without enrichment"), following faradaic ion concentration polarization enhanced assay with the target analyte ("Target and 2° probe, with enrichment"), after regeneration and rinse ("After regeneration"), and after a faradaic ion concentration polarization assay in the absence of the BRAF-Mut target ("2° probe only, with enrichment").

FIG. 22 shows CVCs obtained for a blank solution of Tris.HClO$_4$ buffer only ("Prior to the experiment"), following 60 minutes of exposure to the 0.4 μM 2° probe, 20 pM BRAF-Mut, 20.0 mM Tris.HClO$_4$ buffer assay solution in the absence of enrichment ("Target and 2° probe, without enrichment"), and after 60 minutes of fICP-based enrichment in the assay solution at an applied voltage of 7.0 V ("Target and 2° probe, with enrichment"). The assay solution was flowed through the microchannel at 100 nL min$^{-1}$. After enrichment, a large shift in the CVC is observed, in which the resistance measured in the overlimiting regime is approximately 3-fold lower, indicated by a 3-fold steeper slope of CVC. Such a shift was not observed in the absence of enrichment, which implies that the shift results from electrokinetic enrichment and hybridization of BRAF-Mut to the bioconjugated microbeads.

To control for the effect of the applied voltage on the CVC, CVC following regeneration of the bioconjugated microbeads was evaluated. Following treatment of the BRAF-Mut hybridized microbeads with 0.1 M NaOH solution and a rinse with 20.0 mM Tris.HClO$_4$ buffer, the CVC returned to its initial shape and slope as indicated in FIG. 22 ("After regeneration"). Then a CVC for the fICP-enhanced assay in the absence of the BRAF-Mut target sequence was evaluated and depicted in FIG. 22 ("2° probe only, with enrichment"). No shift in the CVC was observed from that obtained for buffer solution alone ("Prior experiment"). These results indicate that the PSC/Ag/Au device can serve as a sensitive non-optical sensor based on a significant change in its electronic properties following capture of a charged analyte on the PSC bead surface. This sensitive plug-and-play assay, when coupled to a simple electronic readout, becomes a practical platform for detection of nucleic acids at the point of care, and may be extended to other classes of analytes.

Example 6

Electrokinetic Potential Analysis

In this Example, zeta potentials of PSC beads and bioconjugated beads were examined.

100 μL of streptavidin-modified polystyrene microbead ("SV") suspension was rinsed with 100 μL of 20.0 mM Tris.HClO$_4$ buffer by centrifuging the microbeads at 5000 rpm for 3 minutes and decanting the supernatant. Then the SV microbeads were re-suspended in 100 μL of 20.0 mM Tris.HClO$_4$ buffer and used for zeta potential measurements.

100 μL of PSC microbead suspension was rinsed with 100 μL of 20.0 mM Tris.HClO$_4$ buffer by centrifuging the beads at 5000 rpm for 3 minutes and decanting the supernatant. Then the PSC microbeads were re-suspended in 100 μL of 20.0 mM Tris.HClO$_4$ buffer and used for zeta potential measurements.

Biotinylated oligonucleotide with sequence 5'-GTG AGG TCT TCA TGA AGA AAT ATA-3'-Biotin (SEQ ID NO: 5) ("1° probe") was bound to the SV beads as follows. First, 100 μL of the bead suspension was rinsed two times with 100 μL of a wash buffer (20.0 mM Tris.HClO$_4$ buffer, pH 7.5, 1.0 M NaCl, 1.0 mM EDTA, and 0.0005% Triton™ buffer by centrifuging the beads at 5000 rpm for 3 minutes and decanting the supernatant. Lastly, these oligo-bound microspheres hybridized to ssDNA and fluorescently-tagged probe (SV-Biotin-ssDNA-FAM) were re-suspended in 100 μL of 20.0 mM Tris.HClO$_4$ buffer and used for zeta potential measurements.

TABLE 2

| | | Summary of zeta potential measurements. | | |
| Sample | Microbeads | Zeta potential mV | Mobility μm · cm/V · s | Conductivity mS/cm |
|---|---|---|---|---|
| 1 | SV | −28 ± 3 | −2.2 ± 0.2 | 1.29 ± 0.02 |
| 2 | SV-Biotin | −30 ± 2 | −2.4 ± 0.2 | 1.32 ± 0.02 |
| 3 | SV-Biotin-ssDNA | −34 ± 2 | −2.6 ± 0.2 | 1.30 ± 0.03 |
| 4 | SV-Biotin-ssDNA-FAM | −35.0 ± 0.5 | −2.74 ± 0.4 | 1.31 ± 0.03 |
| 5 | PSC | −22 ± 2 | −1.69 ± 0.2 | 1.32 ± 0.02 |

X-100) by centrifuging the beads at 5000 rpm for 3 minutes, and decanting the supernatant. Second, the beads were resuspended into 20 μL of wash buffer and 11.5 μg of 1° probe. The beads were incubated at 300 rpm (ThermoMixer C, Eppendorf, Hauppauge, N.Y.) for 15 min at 20° C. Third, unbound 1° probe was removed by rinsing one time with 100 μL of the wash buffer, and two times with 20 mM Tris.H-ClO$_4$ by centrifuging the beads at 5000 rpm for 3 minutes, and decanting the supernatant. Lastly, these oligo-bound microbeads ("SV-Biotin") were re-suspended in 100 μL of 20 mM Tris.HClO$_4$ buffer and used for zeta potential measurements.

ssDNA (200 base fragment, 5'-TAT ATT TCT TCA TGA AGA CCT CAC AGT AAA AAT AGG TGA TTT TGG TCT AGC TAC AGA GAA ATC TCG ATG GAG TGG GTC CCA TCA GTT TGA ACA GTT GTC TGG ATC CAT TTT GTG GAT GGT AAG AAT TGA GGC TAT TTT TCC ACT GAT TAA ATT TTT GGC CCT GAG ATG CTG CTG AGT TAC TAG AAA GTC ATT GAA GGT CT-3') (SEQ ID NO: 6) was hybridized to SV-Biotin beads according to the following procedure. SV-Biotin beads were prepared according to the procedure described in the preceding paragraph. SV-Biotin beads were then re-suspended in 100 μL of 20 mM Tris.HClO$_4$ buffer containing ssDNA (1.0 nmole) added. The beads were incubated at 300 rpm (ThermoMixer C, Eppendorf, Hauppauge, N.Y.) for 60 minutes at 20° C. Lastly, free ssDNA was removed by rinsing three times with 20 mM Tris.HClO$_4$ buffer, centrifuging the beads at 5000 rpm for 3 minutes and decanting the supernatant after each rinse step. Lastly, these oligo-bound microspheres with hybridized ssDNA ("SV-Biotin-ssDNA") were re-suspended in 100 μL of 20.0 mM Tris.HClO$_4$ buffer and used for zeta potential measurements.

ssDNA and fluorescently-tagged secondary probe (5'-CAT CGA GAT TTC TCT GTA GCT AGA-3'-FAM) (SEQ ID NO: 7) was bound to SV-Biotin beads according to the following procedure. SV-Biotin beads were prepared according to the procedure described in a preceding paragraph. These SV-Biotin beads were then re-suspended in 100 μL of 20.0 mM Tris.HClO$_4$ buffer containing ssDNA (1.0 nmole) and fluorescently-tagged probe (1.7 nmole). The beads were incubated at 300 rpm (ThermoMixer C, Eppendorf, Hauppauge, N.Y.) for 60 minutes at 20° C. Lastly, excess ssDNA and fluorescently-tagged probe were removed by rinsing three times with 20.0 mM Tris.HClO$_4$ Example 7

Voltage Pattern Analysis

In this Example, various voltage patterns for the inlet electrode, the 3D electrode, and the outlet are examined.

Exemplary devices with a 3D electrode of a planar Au microband and Ag microbeads were fabricated according to the invention. The device also includes an upstream secondary bead bed as according to the invention comprising 1° probe-modified SV-Biotin PSC microbeads, modified as described in Example 6.

To facilitate device filling, devices were evacuated in a vacuum desiccator for 20 minutes prior to filling with Tris buffer. Prior to experiments, the microchannels were rinsed for 20 minutes with Tris.HClO$_4$ buffer (20.0 mM, pH 8.3). The reservoirs were then filled with 1.7 μM fluorescently-tagged oligonucleotide (1.7 μM, 5'-CAT CGA GAT TTC TCT GTA GCT AGA-3'-FAM) (SEQ ID NO: 7) in 20.0 mM Tris.HClO$_4$. Next, devices were conditioned at 3.0 V for 5 minutes, at a flow rate of 200 nL min$^{-1}$. The flow rate was then decreased to 100 nL min$^{-1}$ and allowed to equilibrate for 10 minutes. Finally, a driving voltage of 7.0 V was applied. Micrographs demonstrated in FIGS. 28A and 28B were taken 1 minute after applying the driving voltage.

Figure 28A:
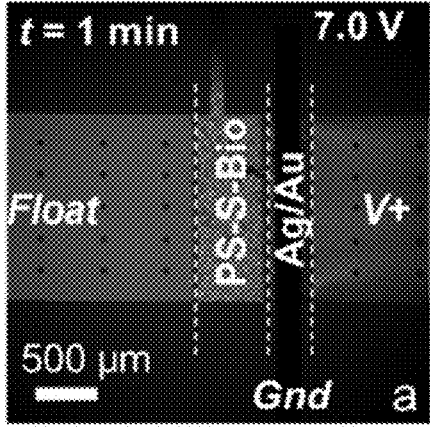
FIG. 28A is a fluorescence micrograph demonstrating ion depletion zone formation and enrichment of fluorescently-tagged oligonucleotide in a secondary bead bed comprising 1° probe-modified polystyrene beads ("PS-S-Bio") after 1 minute following application of 7.0 V to the outlet ("V+"), wherein the 3D electrode is grounded ("Gnd"), and the inlet is floating ("Float").
Figure 28B:
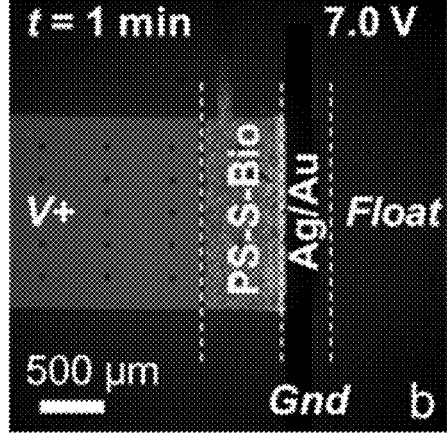
FIG. 28B is a fluorescence micrograph demonstrating ion depletion zone formation and enrichment of fluorescently-tagged oligonucleotide in a secondary bead bed comprising 1° probe-modified polystyrene beads ("PS-S-Bio") after 1 minute following application of 7.0 V to the inlet ("V+"), wherein the 3D electrode is grounded ("Gnd"), and the outlet is floating ("Float").

FIG. 28A depicts a fluorescence micrograph demonstrating IDZ formation and enrichment of fluorescently-tagged oligonucleotide with voltage pattern of Inlet:3D Electrode: Outlet equal to Float:Ground:7.0V, wherein the 3D electrode is grounded ("Gnd"), the inlet is floating ("Float") and the outlet has 7.0 V applied ("V+"). FIG. 28B depicts a similar micrograph but with the outlet floating and 7.0V applied to the inlet for a voltage pattern of 7.0V:Ground:Float.

Example 8

IDZ Formation with 3D Permselective Structures with a Secondary Upstream Bead Bed In this Example, IDZ formation and electrokinetic focusing is confirmed with devices having a 3D permselective structure in the presence of a secondary, upstream PSC bead bed.

Exemplary devices with a 3D permselective structure comprising a Au microband electrode overlaid with cation selective polymer (Nafion™) coated polystyrene microbeads were fabricated according to the invention and to the procedures outlined above. Nafion™ coated polystyrene microbeads were prepared according to the following procedure. First, 100 μL of the polystyrene carboxylate bead suspension was rinsed two times with DDI by centrifuging the microbeads at 5000 rpm for 3 minutes and decanting the supernatant. Then, 100 μL of 5% Nafion™ solution (Ethanol: $H_2O$, 2:1) was added. The microbeads were incubated at 300 rpm, for 45 minutes. Third, microbeads were rinsed two times with 100 μL of DDI by centrifuging the microbeads at 5000 rpm for 3 minutes and decanting the supernatant. Lastly, the Nafion™ coated microbeads ("NB") were resuspended in 100 μL of DDI water.

A suspension of the Nafion™ coated beads in DDI (5.0 μL) was packed into the primary bead bed by pipetting them into the inlet and applying pressure. The inlets of these auxiliary channels were then sealed by adding a drop (approx. 40 μL) of PDMS, which was subsequently cured by incubating the device at 65° C. for 3 hours.

To facilitate device filling, devices were evacuated in a vacuum desiccator for 20 minutes prior to filling with Tris buffer. Prior to experiments, the microchannels were rinsed for 20 minutes with Tris.HClO$_4$ buffer (20.0 mM, pH 8.3). The reservoir was then filled with fluorescently tagged nucleotide (1.7 μM, 5'-CAT CGA GAT TTC TCT GTA GCT AGA-3'-FAM) (SEQ ID NO: 7) in 20.0 mM TrisHClO$_4$. Next, devices were conditioned at 3.0 V for 5 minutes, at a flow rate of 200 nL min$^{-1}$. The flow rate was then decreased to 100 nL min$^{-1}$ and allowed to equilibrate for 10 minutes. Finally, a driving voltage of 7.0 V was applied.

Figure 29:
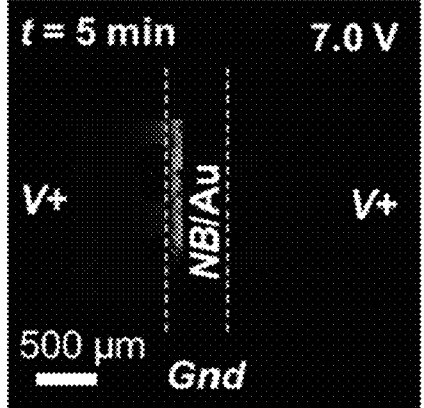
FIG. 29 is a fluorescence micrograph demonstrating ion depletion zone formation and enrichment of fluorescently-tagged oligonucleotide after 5 minutes following application of 7.0 V to the inlet and outlet electrodes wherein the 3D permselective structure comprises Nafion™ coated polystyrene microbeads ("NB").

FIG. 29 depicts a fluorescence micrograph demonstrating IDZ formation and enrichment of fluorescently-tagged oligonucleotide after 5 minutes following application of V+ equal to 7.0 V.

Example 9

Non-Optical Target DNA Detection and Quantification

In this Example, a shift in conductivity in the ohmic region of a CVC is shown to be enhanced by enrichment of target DNA.

Figure 30:
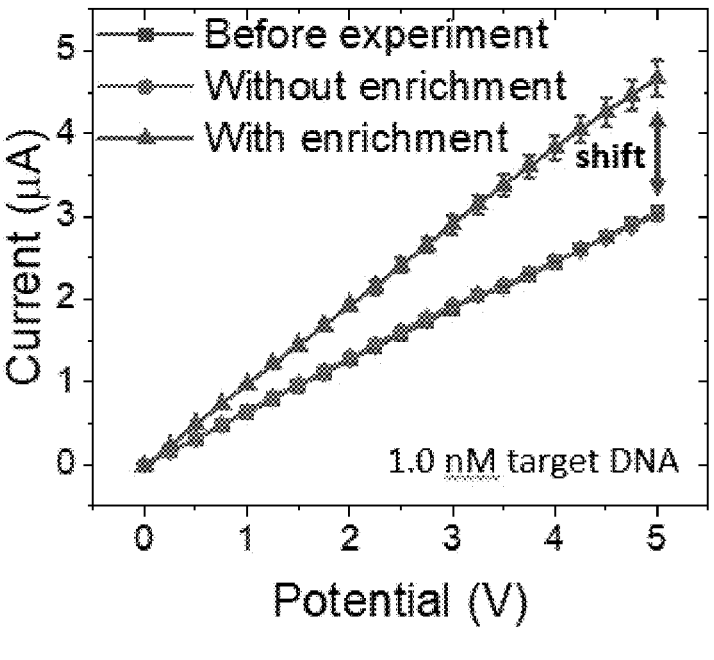
FIG. 30 depicts current-voltage curves obtained before and after sample introduction and then after 30 minutes of target DNA enrichment within a bioconjugated bead bed.

Exemplary devices were fabricated using the processes outlined above, according to FIG. 1, and using the dimensions of Exemplary Device Design 1 in Table 1. CVCs were measured before the experiment, then with and without enrichment, as depicted in FIG. 30. The x-axis, labeled "Potential (V)" is the difference between V1 and V2, which are equal, and V3 which is grounded. The shift in the ohmic region is attributed to an increase in the surface charge of the beads in the secondary bead bed after the target DNA is captured there.

Figure 31:
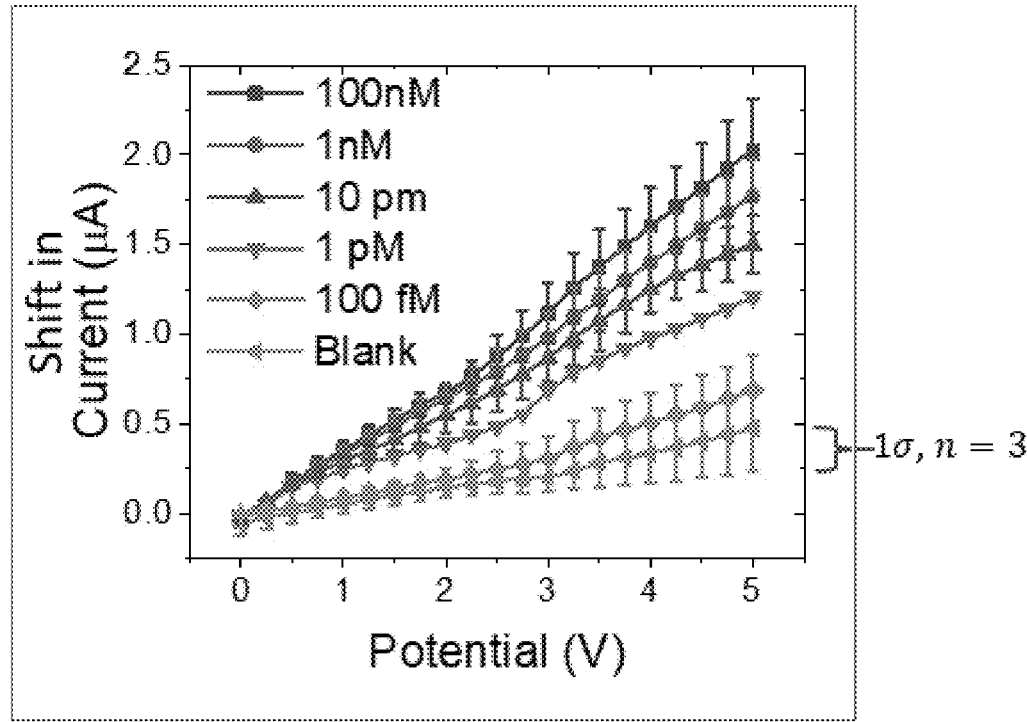
FIG. 31 depicts the shift in current obtained by subtracting current-voltage curves obtained before enrichment from the current-voltage curves obtained after 30 minutes of enrichment for five concentrations of target DNA, and one without target DNA ("Blank").

FIG. 31 shows the shift in current for five different initial concentrations of a target DNA: 100 nM, 1 nM, 10 pM, 1 pM, 100 fM, and one sample without the target DNA ("Blank") after 30 minutes of enrichment. The current shift is obtained by subtracting the CVC before enrichment from the CVC obtained after enrichment. The shift in current in the ohmic region indicates a limit of non-optical detection of 1 pM under these conditions. A longer DNA strand and/or a greater duration of enrichment may further improve the detection limit.

The present disclosure is further defined by the following numbered paragraphs:

1. A microfluidic device comprising:
   one or more fluidic microchannels, wherein the one or more fluidic microchannels are connected to at least one inlet and at least one outlet, wherein a background electrolyte solution is infused through at least one of the inlet(s), flows through the one or more fluidic microchannels, and is withdrawn from at least one of the outlet(s); and at least one flow-through 3D electrode within the microchannel wherein the 3D electrode comprises an electrode and conductive microbeads in a bead bed, wherein
   at least a portion of the conductive microbeads is in contact with the electrode, and wherein at least a portion of the electrode extends outside of the channel for electrical connection,
   wherein at least one of the inlet(s) and at least one of the outlet(s) are each connected to an electrode, and
   wherein the conductive microbeads are contained within a primary bead bed which extends at least a portion of the width and length of the microchannel as defined by a bead bed structure within the microchannel.

2. The device according to paragraph 1, wherein voltage is applied to the inlet and/or outlet electrodes and the 3D electrode for enrichment and separation of charged species at an electric field gradient at the boundary of an ion depleted zone resulting from faradaic processes.

3. A microfluidic device comprising:
   one or more fluidic microchannels, wherein the one or more fluidic microchannels are connected to at least one inlet and at least one outlet, wherein a background electrolyte solution is infused through at least one of the inlet(s), flows through the one or more fluidic microchannels, and is withdrawn from at least one of the outlet(s); and
   at least one flow-through 3D permselective structure comprising an electrode and permselective membrane coated microbeads in a bead bed, wherein at least a portion of the permselective membrane coated microbeads is in contact with the electrode, and wherein at least a portion of the electrode extends outside of the channel for electrical connection,
   wherein at least one of the inlet(s) and at least one of the outlet(s) are each connected to an electrode, and
   wherein the permselective membrane coated microbeads are contained within a primary bead bed defined by a bead bed structure within the microchannel.

4. The device according to paragraph 3, wherein voltage is applied to the inlet and/or outlet electrodes and the 3D permselective structure for enrichment and separation of charged species at an electric field gradient at the boundary of an ion depleted zone resulting from ion concentration polarization.

5. The device of any one of paragraphs 1 to 4, wherein the one or more fluidic microchannels have a width of about 0.025 mm to about 20 mm, a height of about 5 μm to about 2000 μm, and a length of about 0.5 mm to about 100 mm.

6. The device of any one of paragraphs 1 to 5, wherein the flow-through 3D electrode or 3D permselective structure is placed along the midpoint inside the one or more fluidic microchannels.

7. The device of any one of paragraphs 1 to 5 wherein the flow-through 3D electrode or 3D permselective structure is placed about three-quarters of the distance from at least one of the inlets and at least one of the outlets.

8. The device of any one of paragraphs 1 to 7, wherein the device has more than one microchannel and wherein the microchannels are connected to the same inlet and the same outlet, or several distinct inlets and several distinct outlets, and wherein each microchannel has at least one flow-through 3D electrode and/or 3D permselective structure, and wherein each flow-through 3D electrode or 3D permselective structure has a separate electrical contact.

9. The device of any one of paragraphs 1 to 8, wherein the microchannel further comprises at least one secondary bead bed of microbeads, wherein the microbeads are contained within the secondary bead bed defined by a bead bed structure within the microchannel.

10. The device of paragraph 9, wherein the secondary bead bed is located upstream from the flow-through 3D electrode or 3D permselective structure.

11. The device of any one of paragraphs 9 to 10, wherein the microbeads in the secondary bead bed are not conductive.

12. The device of any one of paragraphs 9 to 11, wherein the microbeads in the secondary bead bed are bioconjugated.

13. The device of paragraph 12 wherein the bioconjugated microbeads comprise biotin binding proteins bound with biotinylated molecules comprising one or more DNA probes.

14. The device of any one of paragraphs 1 to 13, wherein the microbeads enter the bead bed and/or secondary bead bed through auxiliary channel(s) that are sealed prior to device usage.

15. The device of any one of paragraphs 9 to 14, wherein the microfluidic device has more than one microchannel and wherein the microchannels are connected to the same inlet and the same outlet, or several distinct inlets and several distinct outlets, and wherein each channel has a secondary bead bed each comprised of a different set of microbeads.

16. The device of paragraph 15, wherein the microbeads in each secondary bead bed comprise biotinylated molecules comprising DNA probes such that the DNA probes in each secondary bead bed target different nucleic acids.

17. The device of any one of paragraphs 1 to 16, wherein the bead bed structure comprises bead bed posts wherein the bead bed posts extend from the floor of the microchannel and are spaced such that the microbeads are contained within the area defined by the bead bed posts.

18. The device of paragraph 17, wherein the bead bed posts have a diameter or a cross-section of from about 2 $\mu$m to about 500 $\mu$m, and the gaps between the bead bed posts are from about 1 $\mu$m to about 250 $\mu$m.

19. The device of any one of paragraphs 1 to 18, wherein the bead bed structure comprises a weir structure, a porous matrix, a chemical linker, or combination thereof 20. The device of any one of paragraphs 1 to 19, wherein the bead bed extends the length of the microchannel from about 0.025 mm to about 5 mm.

21. The device of any one of paragraphs 1 to 20, wherein the device further comprises a power source connected with the inlet electrode and/or the outlet electrode and/or the 3D electrode and/or the 3D permselective structure, wherein the power source is configured to supply a voltage in the range of from about 1 V to about 500 V.

22. The device of paragraph 21, wherein the power source is a battery.

23. The device of any one of paragraphs 1 to 22, wherein the 3D electrode and/or the 3D permselective structure comprises a planar microband electrode.

24. The device of paragraph 23, wherein the planar microband electrode extends the length of the microchannel from about 0.005 mm to about 5 mm, and is from about 0.05 $\mu$m to about 1 $\mu$m thick.

25. The device of any one of paragraphs 1 to 22, wherein the 3D electrode and/or the 3D permselective structure comprises a rod, a wire, a pin, or combinations thereof.

26. The device of paragraph 25, wherein the rod, wire, and/or pin has a diameter of from about 0.05 mm to about 2 mm.

27. The device of any one of paragraphs 1 to 26, wherein the 3D electrode and/or the 3D permselective structure comprises a conductive epoxy, an ionic liquid, or combinations thereof.

28. The device of any one of paragraphs 1 to 27, wherein the microbeads in the 3D electrode and/or 3D permselective structure have a diameter of from about 1 $\mu$m to about 500 $\mu$m, preferably from about 10 $\mu$m to about 20 $\mu$m.

29. The device of any of paragraphs 23 to 24, wherein the planar microband electrode is comprised of Au and the microbeads in the 3D flow-through electrode are comprised of Ag.

30. The device of any of paragraphs 3 to 29, wherein the permselective membrane coated microbeads in the 3D permselective structure are coated with an ion permselective membrane.

31. The device of any one of paragraphs 9 to 30, wherein the diameter of the microbeads in the secondary bead bed is from about 1 $\mu$m to about 500 $\mu$m.

32. The device of any one of paragraphs 9 to 31, wherein the microbeads in the secondary bead bed comprise polystyrene carboxylate and have a diameter of from about 10 $\mu$m to about 16 $\mu$m.

33. The device of any one of paragraphs 1 to 32, wherein the background electrolyte solution comprises a buffer.

34. The device of any one of paragraphs 1 to 33, wherein the background electrolyte solution comprises a biological sample.

35. A method of focusing at least one charged species from a background electrolyte solution comprising:

flowing the background electrolyte solution containing targeted charged species through the microchannel(s) of the microfluidic device of any one of paragraphs 1 to 34;

applying a voltage to the electrodes at the inlet and/or outlet of the device and/or the 3D electrode and/or the 3D permselective structure for a period of time so the targeted charged species is focused along the electric field gradient at the boundary of an ion depleted zone created by the 3D electrode or 3D permselective structure.

36. A method of focusing at least one charged species from a background electrolyte solution comprising:

flowing the background electrolyte solution containing a targeted charged species through the microchannels of the microfluidic devices of any one of paragraphs 9 to 34;

applying a voltage to the electrodes at the inlet and/or outlet of the device and/or the 3D electrode and/or the 3D permselective structure for a period of time so the targeted charged species is focused at the strong electric field at the edge of an ion depleted zone created by the 3D electrode or 3D permselective structure so the targeted charged species is focused within the secondary bead bed.

37. The method of any one of paragraphs 35 to 36, further comprising optical detection of the at least one targeted charged species at the ion depleted zone.

38. The method of paragraph 37, wherein the optical detection is obtained by fluorescence imaging, colorimetry, infrared absorption spectroscopy, ultraviolet absorption spectroscopy, radiometric imaging, Raman spectroscopy, or combinations thereof 39. The method of any one of paragraphs 35 to 38, further comprising non-optical detection of the at least one targeted charged species at the ion depleted zone.

40. The method of paragraph 39, wherein the non-optical detection of enrichment of a targeted charged species is obtained by a change in impedance.

41. The method of paragraph 40, wherein the change in impedance is observed by a shift in slope in a current voltage curve at the 3D electrode and/or the 3D permselective structure.

42. The method of paragraph 40, wherein the change in impedance is observed by a shift in absolute current at a given voltage at the 3D electrode and/or the 3D permselective structure.

43. The method of paragraph 40, wherein the change in impedance is observed by electrochemical impedance spectroscopy at a voltage in the overlimiting region of the 3D electrode and/or the 3D permselective structure.

44. The method of any one of paragraphs 35 to 43, wherein the targeted charged species is a nucleic acid, protein, antigen, antibody, bioparticle, bacteria, virus, other biomolecule, or combinations thereof 45. The method of any one of paragraphs 35 to 44, wherein the background electrolyte solution has a volumetric flow rate from about 0 mL min' to about 1 mL min$^1$.

46. The method of any one of paragraphs 35 to 45, wherein the method occurs at the point of care.

47. The method of any one of paragraphs 35 to 46, wherein the electrode at the outlet is set at 0 V, the electrode at the inlet is set from about 250 mV to about 500 V, and the applied voltage at the 3D electrode is set such that a sufficient fraction of the current at the inlet is redirected to the outlet to avoid overly high current density at the 3D electrode.

48. The method of any one of paragraphs 35 to 47, wherein the throughput is from about 0.001 mL/hour to about 60 mL/h.

49. The method of any one of paragraphs 35 to 48, wherein the enrichment of a targeted charged species is at least about 300-fold in about 60 minutes.

50. The method of any one of paragraphs 35 to 49, where in the method occurs at the point of care, and wherein the background electrolyte solution is a biological sample.

Having thus described in detail various embodiments of the present disclosure, it is to be understood that the present disclosure defined by the above numbered paragraphs is not to be limited to particular details set forth in the above description as many apparent variations thereof are possible without departing from the spirit or scope of the present disclosure.

While this invention may be embodied in many different forms, the described scientific papers and other referenced materials mentioned herein are incorporated by reference in their entirety. Furthermore, the invention encompasses any possible combination of some or all of the various embodiments mentioned herein, described herein and/or incorporated herein. In addition, the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the following claims where the term "comprising" means "including, but not limited to". Those familiar with the art may recognize other equivalents to the specific embodiments described herein which equivalents are also intended to be encompassed by the following claims.

---

What is claimed is:

1. A microfluidic device comprising:

one or more fluidic microchannels, wherein the one or more fluidic microchannels are connected to at least one inlet and at least one outlet, wherein a background electrolyte solution is infused through at least one of the inlet(s), flows through the one or more fluidic microchannels, and is withdrawn from at least one of the outlet(s); and at least one flow-through 3D electrode within the one or more fluidic microchannel wherein the 3D electrode comprises an electrode and microbeads, wherein the microbeads are contained within a primary bead bed which extends at least a portion of the width and length of the microchannel as defined by a bead bed structure within the one or more fluidic microchannel; and at least one bead-based assay comprising a secondary bed of microbeads, wherein the microbeads in the second-ary bead bed are magnetic, comprise conductive or semi-conductive material, and/or are bioconiugated; wherein the microbeads are contained within the sec-ondary bead bed defined by a bead bed structure within the microchannel, and wherein the bead-based assay is located upstream from the 3D electrode;

wherein at least one of the inlet(s) and/or at least one of the outlet(s) are connected to an inlet electrode and/or an outlet electrode, and wherein the microbeads are contained within a primary bead bed which extends at least a portion of the width and length of the microchannel as defined by a bead bed structure within the one or more fluidic microchannel.

2. The device according to claim 1, wherein at least a portion of the microbeads in the primary bead bed is in contact with the electrode in the flow-through 3D electrode, and wherein at least a portion of said electrode extends outside of the channel for electrical connection.

3. The device according to claim 1, wherein the microbeads in the primary bead bed are conductive microbeads and voltage is applied to the inlet electrode and/or the outlet electrode and the 3D electrode for enrichment and separation of charged species at an electric field gradient at the boundary of an ion depleted zone resulting from faradaic processes.

4. The device according to claim 1, wherein the microbeads in the primary bead bed are permselective membrane coated microbeads and voltage is applied to the inlet electrode and/or the outlet electrode and the 3D electrode for enrichment and separation of charged species at an electric field gradient at the boundary of an ion depleted zone resulting from ion concentration polarization.

5. The device of claim 1, wherein the one or more fluidic microchannels have a width of about 0.025 mm to about 20 mm, a height of about 5 μm to about 2000 μm, and a length of about 0.5 mm to about 100 mm.

6. The device of claim 1, wherein the device has more than one microchannel and wherein the microchannels are connected to the same inlet and the same outlet, or several distinct inlets and several distinct outlets, and wherein each microchannel has at least one flow-through 3D electrode, and wherein each flow-through 3D electrode has a separate electrical contact.

7. The device of claim 1, wherein the microbeads in the secondary bead bed are bioconjugated comprising biotin binding proteins bound with biotinylated molecules comprising one or more DNA probes.

8. The device of claim 1, wherein the microfluidic device has more than one microchannel and wherein the microchannels are connected to the same inlet and the same outlet, or several distinct inlets and several distinct outlets, and wherein each channel has a secondary bead bed each comprised of a different set of microbeads.

9. The device of claim 8, wherein the microbeads in each secondary bead bed comprise biotinylated molecules comprising DNA probes such that the DNA probes in each secondary bead bed target distinct nucleic acids.

10. The device of claim 1, wherein the device further comprises a power source connected with the inlet electrode and/or the outlet electrode and/or the 3D electrode, wherein the power source is configured to supply a voltage in the range of from about 1 V to about 500 V.

11. The device of claim 1, wherein the 3D electrode comprises a planar electrode, a rod, a wire, a pin, a conductive epoxy, an ionic liquid, or combinations thereof.

12. The device of claim 3, wherein the microbeads in the 3D flow-through electrode comprise Ag, Au, Ni, Fe, C, Pt, a conductive polymer, an insulator coated with a conductor, a magnetic bead with a conductive coating, and combinations thereof.

13. The device of claim 4, wherein the permselective membrane coated microbeads in the 3D electrode are coated with an ion permselective membrane.

14. A method of focusing at least one charged species from a background electrolyte solution comprising:

flowing the background electrolyte solution containing targeted charged species through the microchannel(s) of the microfluidic device of claim 1;

applying a voltage to the electrode at the inlet and/or outlet of the device and/or the 3D electrode for a period of time so the targeted charged species is focused along the electric field gradient at the boundary of an ion depleted zone created by the 3D electrode.

15. A method of focusing at least one charged species from a background electrolyte solution comprising:

flowing the background electrolyte solution containing a targeted charged species through the microchannels of the microfluidic devices of claim 1;

applying a voltage to the electrodes at the inlet and/or outlet of the device and/or the 3D electrode for a period of time so the targeted charged species is focused at the strong electric field at the edge of an ion depleted zone created by the 3D electrode so the targeted charged species is focused within the secondary bead bed.

16. The method of claim 14, further comprising optical detection of the at least one targeted charged species at the ion depleted zone, wherein the optical detection comprises fluorescence imaging, colorimetry, infrared absorption spectroscopy, ultraviolet absorption spectroscopy, radiometric imaging, Raman spectroscopy, or combinations thereof.

17. The method of claim 14, further comprising non-optical detection of the at least one targeted charged species at the ion depleted zone, wherein the non-optical detection of enrichment of a targeted charged species comprises a change in impedance.

18. The method of claim 14, wherein the enrichment of a targeted charged species is at least about 300-fold in about 60 minutes.

19. The method of claim 14, wherein the method occurs at the point of care, and wherein the background electrolyte solution is a biological sample.

* * * * *